(12) United States Patent
Krastev

(10) Patent No.: US 9,498,308 B1
(45) Date of Patent: Nov. 22, 2016

(54) MULTI-FUNCTIONAL OSTEOTOME AND METHOD OF USE FOR SINUS LIFT PROCEDURE

(71) Applicant: Pavel Krastev, New Hyde Park, NY (US)

(72) Inventor: Pavel Krastev, New Hyde Park, NY (US)

( * ) Notice: Subject to any disclaimer, the term of this patent is extended or adjusted under 35 U.S.C. 154(b) by 294 days.

(21) Appl. No.: 14/033,031

(22) Filed: Sep. 20, 2013

Related U.S. Application Data

(63) Continuation-in-part of application No. 13/942,920, filed on Jul. 16, 2013.

(60) Provisional application No. 61/674,121, filed on Jul. 20, 2012, provisional application No. 61/703,838, filed on Sep. 21, 2012, provisional application No. 61/714,345, filed on Oct. 16, 2012.

(51) Int. Cl.
| | |
|---|---|
| *A61C 8/00* | (2006.01) |
| *A61B 1/00* | (2006.01) |
| *A61B 1/05* | (2006.01) |
| *A61B 1/24* | (2006.01) |
| *A61C 1/07* | (2006.01) |
| *A61C 17/02* | (2006.01) |
| *A61C 3/03* | (2006.01) |

(52) U.S. Cl.
CPC .......... *A61C 8/0092* (2013.01); *A61B 1/00087* (2013.01); *A61B 1/05* (2013.01); *A61B 1/24* (2013.01); *A61C 1/07* (2013.01); *A61C 3/03* (2013.01); *A61C 17/0202* (2013.01)

(58) Field of Classification Search
CPC ................................................... A61C 8/0092
See application file for complete search history.

(56) References Cited

U.S. PATENT DOCUMENTS 3,924,493 A * 12/1975 Penner ................ B25B 23/0035
 279/79
4,508,005 A   4/1985 Herman
(Continued)

FOREIGN PATENT DOCUMENTS

WO    WO2004/043303    5/2004

OTHER PUBLICATIONS

Vladimir Koifman, "Fraunhofer Institute and Awaiba Developed 1 mm>3 Camera," Image Sensors World, News and Discussions about Image Sensors, Mar. 11, 2011, http://image-sensors-world.blogspot.com/2011/03/fraunhofer-institute-and-awaiba.html.

(Continued)

*Primary Examiner* — Ralph Lewis
(74) *Attorney, Agent, or Firm* — Thomas A. O'Rourke; Rodner & O'Rourke, LLP

(57) ABSTRACT

A device, for atraumatically elevating the Schneiderian membrane during a sinus lift procedure with positive, real-time indication of the amount of lift occurring, may include: a first conduit; a first balloon coupled to a first end of the first conduit and in fluid communication therewith; a second conduit; a second balloon coupled to a first end of the second conduit and in fluid communication therewith; and means for infusing a fluid into the first and second conduits to cause inflation of the balloons. The balloons may be constructed the same, or may be individually tailored. The first balloon is configured to be received within the implant socket and apply pressure to the membrane. The second balloon, expanding against atmospheric pressure only, is configured of a different material and wall thickness. An integral scale behind the second balloon provides indication of the inflation and lift provided by the first balloon.

12 Claims, 37 Drawing Sheets

(56) References Cited

U.S. PATENT DOCUMENTS

| | | | |
|---|---|---|---|
| 5,514,113 A | 5/1996 | Anderson | |
| 5,685,716 A | 11/1997 | Linkow | |
| 6,171,312 B1 | 1/2001 | Beaty | |
| 6,695,847 B2 * | 2/2004 | Bianchetti | A61B 17/1688 606/53 |
| 7,125,253 B2 | 10/2006 | Kitamura | |
| 7,364,430 B2 * | 4/2008 | Kitamura | A61C 8/0092 433/167 |
| 7,396,232 B2 | 7/2008 | Fromovich | |
| 7,632,280 B2 | 12/2009 | Hochman | |
| 7,771,199 B2 | 8/2010 | Hochman | |
| 7,934,929 B2 * | 5/2011 | Better | A61C 8/0018 433/173 |
| 8,029,284 B2 * | 10/2011 | Better | A61C 8/0018 433/173 |
| 8,075,564 B2 | 12/2011 | Lee | |
| 8,083,747 B2 | 12/2011 | Song | |
| 8,366,443 B2 * | 2/2013 | Nahlieli | A61B 1/247 433/172 |
| 2006/0172255 A1 * | 8/2006 | Hochman | A61C 8/0089 433/144 |
| 2007/0042326 A1 | 2/2007 | Cardoso | |
| 2008/0275379 A1 | 11/2008 | Kurrek | |
| 2008/0293010 A1 * | 11/2008 | Song | A61C 8/0089 433/165 |
| 2009/0042158 A1 | 2/2009 | Steiner | |
| 2009/0274996 A1 | 11/2009 | Miller | |
| 2009/0292288 A1 | 11/2009 | Hung | |
| 2009/0326440 A1 | 12/2009 | Lee | |
| 2010/0221681 A1 | 9/2010 | Hochman | |
| 2010/0291511 A1 | 11/2010 | Lee | |
| 2010/0324561 A1 | 12/2010 | Watzek | |
| 2014/0038126 A1 * | 2/2014 | Krastev | A61C 19/04 433/75 |

OTHER PUBLICATIONS

Muronoi M, Xu H, Shimizu Y, and Ooya K., "Simplified procedure for augmentation of the sinus floor using a haemostatic nasal balloon," British Journal of Oral & Maxillofacial Surgery 41(2):120-121, 2003.

* cited by examiner

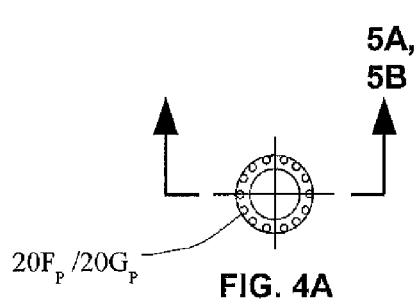
FIG. 4A
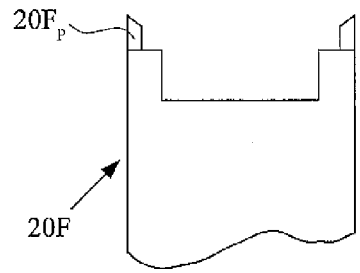
FIG. 4B
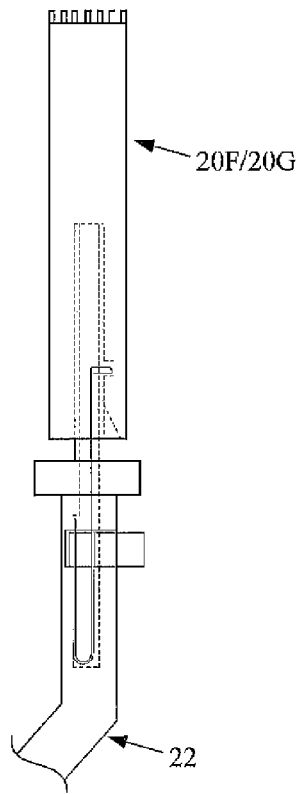
FIG. 4
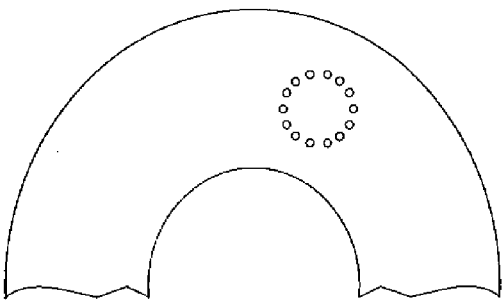
FIG. 4C
FIG. 4D

FIG. 6D  FIG. 6C  FIG. 6B  FIG. 6A
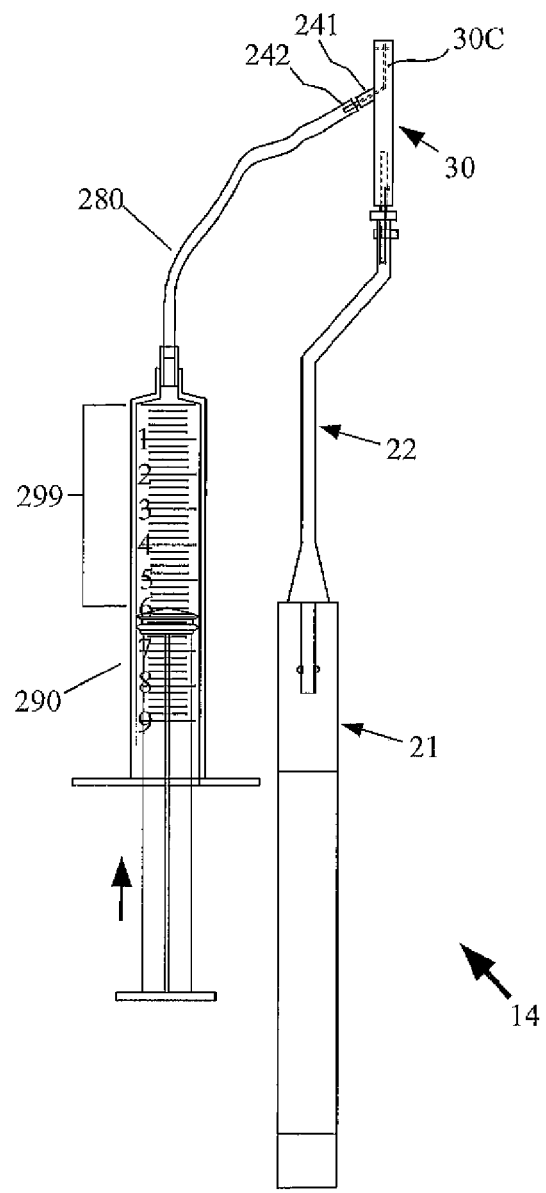
FIG. 6

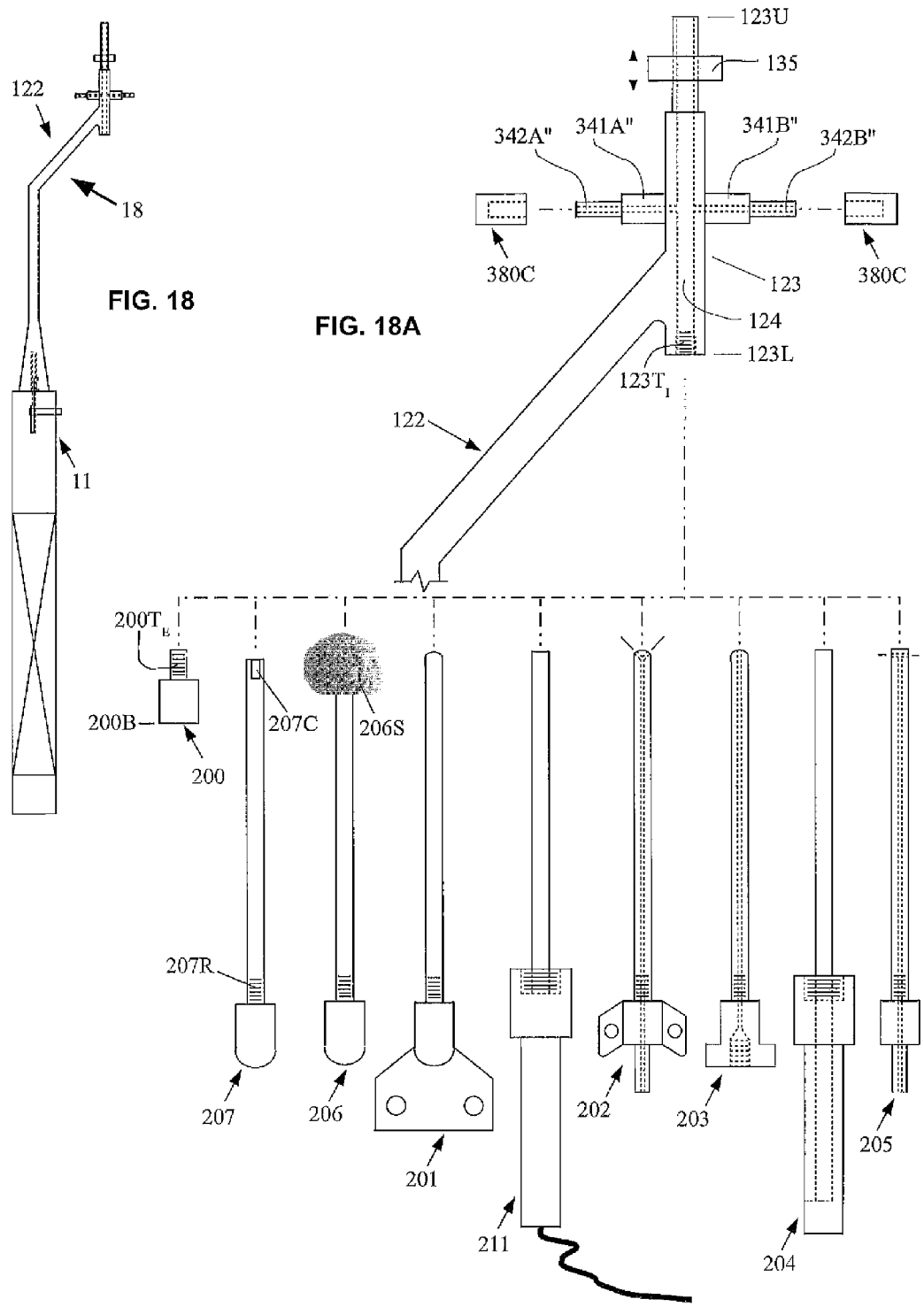

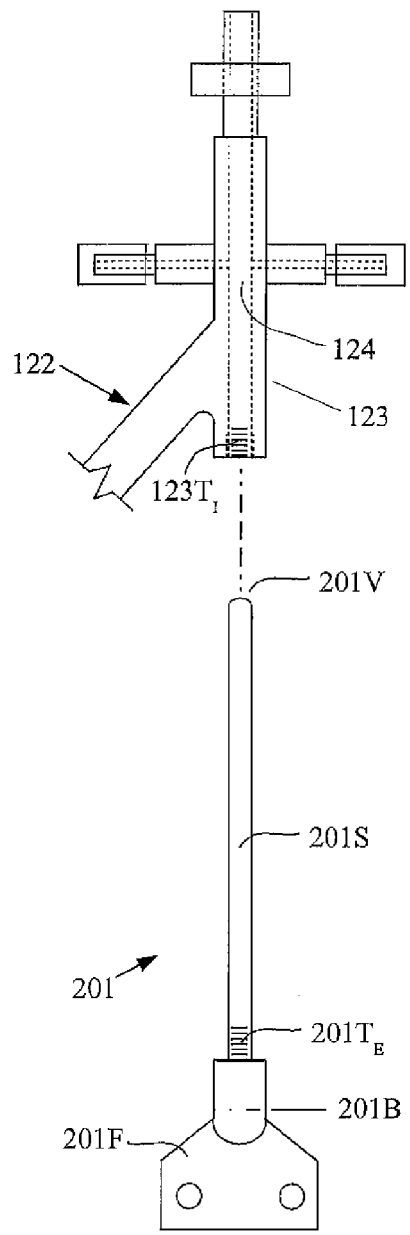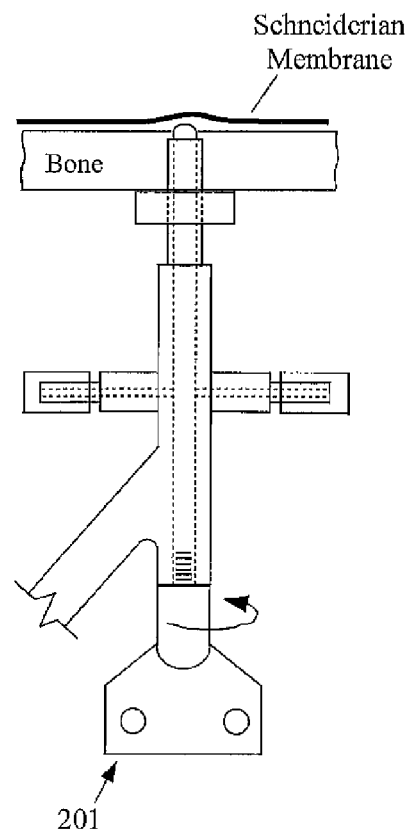
FIG. 19
FIG. 19A

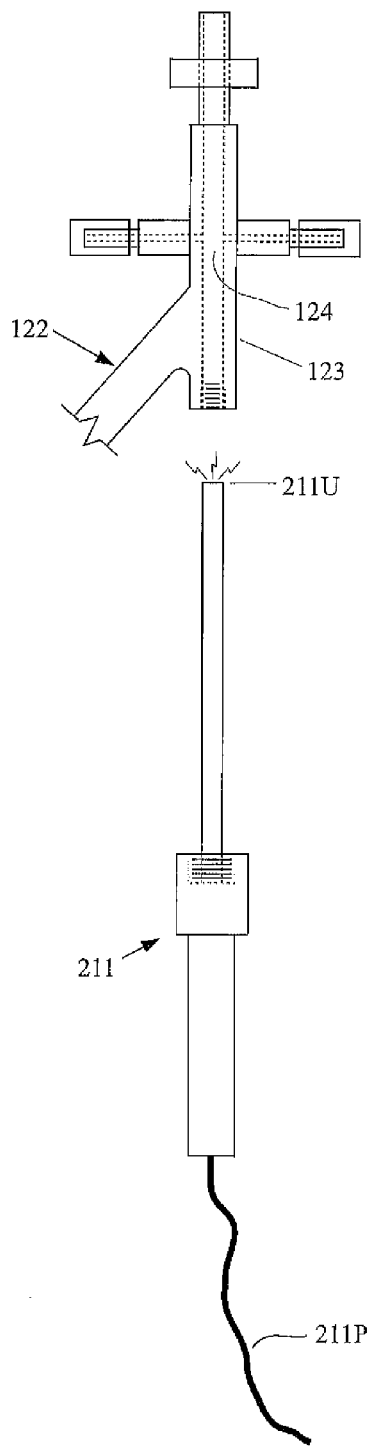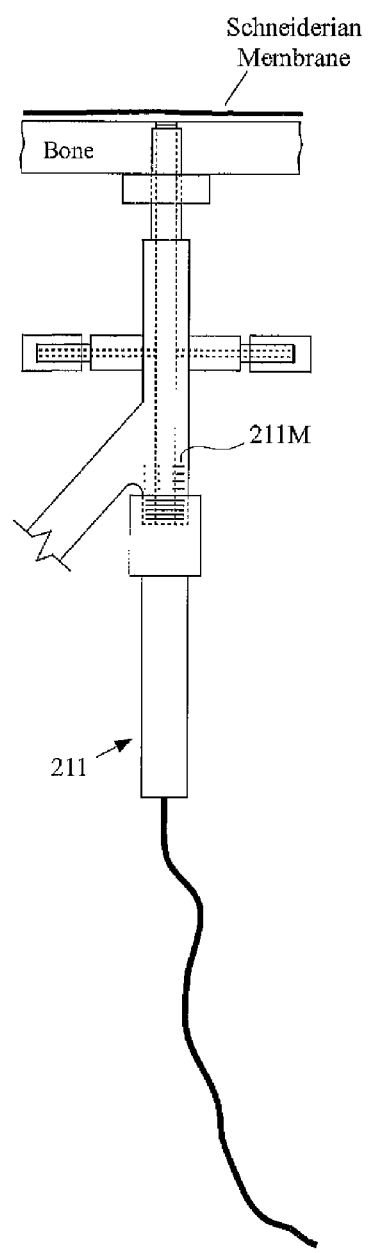
FIG. 19C
FIG. 19B

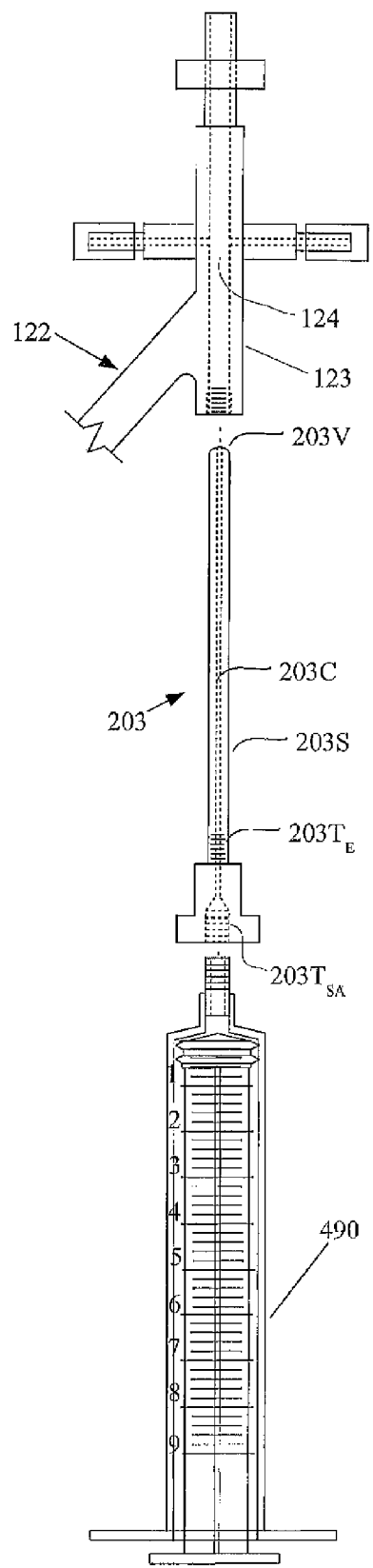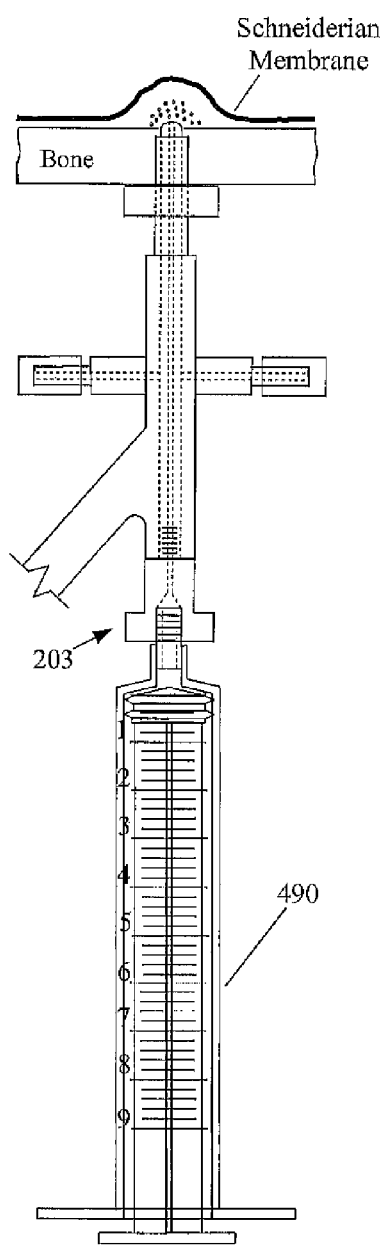
FIG. 21A
FIG. 21

MULTI-FUNCTIONAL OSTEOTOME AND METHOD OF USE FOR SINUS LIFT PROCEDURE

CROSS REFERENCES TO RELATED APPLICATIONS

This application is a continuation-in-part of U.S. application Ser. No. 13/942,920 filed on Jul. 16, 2013, which claims priority on U.S. Provisional Application Ser. No. 61/674,121, titled "Improved Apparatus and Method for Sinus Lift Procedure," filed on Jul. 20, 2012, and this application claims priority on U.S. Provisional Application Ser. No. 61/703,838, titled "Multi-Functional Osteotome and Method of Use for Sinus Lift Procedure," filed on Sep. 21, 2012, and claims priority on U.S. Provisional Application Ser. No. 61/714,345, filed on Oct. 16, 2012, with the disclosures of each being incorporated herein by reference.

FIELD OF THE INVENTION

The present invention relates to improvements in Osteotomes for performing crestal approach sinus lift procedures, and more particularly to improvements that reduce the number of separate tools that must be obtained and utilized by the dental specialist, as well as improvements that better facilitate completing the procedure more safely.

BACKGROUND OF THE INVENTION

There are many conditions which may result in a person becoming partially or completely edentulous (periodontal disease, an injury, etc.), which in the past had been remedied by the wearing of a prosthetic device known as dentures. Dentures were constructed to replace the missing teeth and were supported by surrounding teeth and/or by the underlying tissue. The significant drawbacks to the wearing of such partial or complete dentures, principally its means of support, which often required the use of adhesives and its cleaning requirements, had served to bolster the development of dental implants.

Dental implants may be subperiosteal, being placed on top of the bone and beneath the periostium—the fibrous membrane covering the jaw bones—and may have posts protruding through the gum to support a prosthesis. Alternatively, a dental implant may be endosteal (in the bone—endosseous), being a "root" device that is usually made of titanium, which is inserted into the jaw through the bone at the alveolar ridges. A healing period on the order of months is necessary for osseointegration, during which time the bone will grow in and around the implant to provide support that may exceed that of the natural tooth. After the healing period, an abutment may be attached thereto and may protrude through the periostium and gingival tissues to receive a prosthodontic appliance—a new tooth. Endosteal implants are used within wide and deep bone, or bone at least wide enough for their placement. Where the jaw bone is too narrow and not a good candidate for endosseous implants, a subperiosteal implant may be utilized. However, the subperiosteal implant technique is seldom used today.

The alveolar ridges are columns of bone, found on both the maxilla and the mandible, that surround and anchor the teeth within sockets known as alveoli. However, the alveolar bone quickly becomes atrophic in the absence of teeth, resulting in lack of available bone. In the Maxilla, sinus pneumatization decreases available bone after tooth loss, requiring a sinus elevation procedure prior to implant placement. Studies have shown the bone loss to be progressive. In many cases where a patient's jaw bone may have become too shallow or narrow for an endosteal implant, a sinus lift procedure may be performed to increase the amount of bone in the maxilla. The sinus lift procedure may be performed either through a lateral approach or a crestal approach.

In the crestal approach for a sinus lift procedure of the posterior maxilla (upper jaw), to which the improvements of the present invention is directed, a pilot drill may initially be used to create a small hole to form an implant insertion axis. The depth of penetration by the drill may be limited, by a stop or guide that is set using x-rays of the crestal area, so as to be within 1-2 mm of the sinus floor. The anatomical characteristics of the posterior maxilla, particularly the existence of its more spongy (cancellous) bone, enable it to successfully lend itself to undergo the ridge expansion osteotomy technique developed by R. B. Summers, which was published in 1994 (see e.g., Summers, D M D, Robert B, "A New Concept in Maxillary Implant Surgery: The Osteotome Technique;" 1994; Summers, D M D, Robert B, "The Osteotome Technique: Part 2—The Ridge Expansion Osteotomy (REO) Procedure;" 1994; and Summers, D M D, Robert B, "The Osteotome Technique: Part 3—Less Invasive Methods of Elevating the Sinus Floor;" 1994).

The technique causes expansion of the pilot hole without further elimination of bone material, and generally compresses the bone and increases bone density, in the surgeon's favor. The technique uses a succession of conical expansion Osteotome tools having a gradual diameter escalation. The smallest caliber expansion Osteotome tool is inserted manually into the pilot hole, with pressing and rotating of the tool occurring until the desired depth is reached, or until further penetration is resisted, at which time gentle tapping using a surgical mallet on the Osteotome may cause it to reach the proper depth. Further use of successively larger Osteotome tools causes lateral compression that increases bone density and the size of the opening. The different calibers of Osteotomes may be constructed such that the initial diameter of a successively larger Osteotome is the same as the largest penetrating diameter of the previous conical Osteotome that was used, thereby providing a constant progression of increasing separation.

During the expansion of the opening, with its resulting bone compression using the succession of Osteotomes, care must be taken as to the depth of penetration by the tools, to avoid puncturing of the sinus membrane. Once sufficient expansion and compaction has occurred for the intended implant, the cortical bone layer of the inferior sinus wall (floor) may be intentionally breached using the Osteotome, while exercising diligence to again avoid damage to the sinus membrane. The membrane is then typically detached in a gentle manner and displaced inwardly (lifted) using the Osteotome to working height. The space caused by the displacement of the membrane that had been overlying the sinus floor may then be packed with small donor bone particles using a larger diameter tool. The particles become part of the patient's jawbone during the osseointegration process. The implant is generally inserted into the new "socket" immediately, when enough bone height is present to achieve good primary fixation. If there was initially insufficient bone between the upper jaw ridge and the sinus membrane to provide adequate stability for the implant, the sinus augmentation and implant placement may need to be performed in separate procedures, being separated by the passage of several months.

There are many steps taken during the performance of this procedure during which serious damage may be caused to the patient's physiology, particularly with respect to the sinus membrane. Puncturing of the membrane is a serious complication, which may be worsened by the introduction of bone particles therein, and the contracting of a fungal infection could furthermore be fatal. In addition, when a perforation occurs, the bone particle may lead to blockage of the osteum and cause sinusitis. If membrane repair cannot be carried out, the procedure should be aborted prior to bone placement. Membrane repair during the crestal approach is very difficult to achieve.

The prior art Osteotomes have sought to improve the procedure, but are nonetheless still lacking. For example, U.S. Patent Application Pub. No. 2009/0292288 by Hung discloses that "tip members . . . with different styles and sizes" may be replaceable "by a mechanical manner such as screwing." While constituting an improvement, it does not go far enough to assist the oral surgeon seeking to perform implant surgery on a patient in a brief amount of time, and in the safest manner according to his/her own physique and preferences. The present invention improves upon the Hung application.

The various improvements offered by the present invention serve to reduce the number of Osteotomes that are required by the oral surgeon, and additionally provide new apparatus that increase safety as to preventing the perforation of the sinus membrane, and for performing the sinus lift procedure.

OBJECTS OF THE INVENTION

It is an object of the invention to provide an Osteotome capable of compressing bone, as the diameter of a straight or tapered tip is malleted to working length.

It is a further object of the invention to provide an improved multi-functional Osteotome that reduces the number of separate instruments required, by permitting various tips enabling various different functionality, to be releasably secured to a specially adapted handle member.

It is another object of the invention to provide an Osteotome tip that incorporates a balloon, for use in elevating the sinus membrane.

It is a further object of the invention to provide an improved Osteotome tip that incorporates a redundant balloon arrangement, having a first balloon for use in atraumatic sinus membrane elevation and a second balloon for providing a visual indication to the oral surgeon, as to the extent of balloon deployment that has occurred within the sinus cavity.

It is a further object of the invention to provide an improved Osteotome that permits the oral surgeon to checks if the sinus floor has been infractured by attempting to inject a flow of saline solution.

It is another object of the invention to provide a means of supplying a measured amount of saline solution within an implant hole to more safely cause lifting of the schneiderian membrane.

It is a further object of the invention to provide a dual port means of controlling both the amount of saline solution delivered under the displaced schneiderian membrane, and of measuring the amount of saline solution evacuated therefrom.

It is a further object of the invention to provide a means of quickly comparing the amount of evacuated saline solution with the amount of solution originally delivered through the implant hole to raise the sinus membrane.

It is another object of the invention to provide a pressure relief valve within a saline solution delivery system for an implant hole to permit the escape of saline solution with an excessive pressure gradient that risks membrane perforation.

It is a further object of the invention to provide an improved Osteotome which is adapted to receive various geometry nozzles, to allow gentle separation of the sinus membrane.

It is also an object of the invention to provide a means of supplying a measured amount of saline solution within an implant hole, and of porting the saline solution withdrawn therefrom into a volumetric measuring means to verify sinus membrane integrity.

Further objects and advantages of the invention will become apparent from the following description and claims, and from the accompanying drawings.

BRIEF DESCRIPTION OF THE DRAWINGS

FIG. 4 illustrates securing of one of the tips for perforating the cortical layer, from FIG. 3C, being releasably received by the handle and support member of FIG. 1.

FIG. 4A is a top view of the tip used in FIG. 4.

FIG. 4B is a section cut through the tip of FIG. 4, illustrating a first embodiment of the prongs in which they are each shaped to form a point.

FIG. 4C is a section cut through the tip of FIG. 4, illustrating a second embodiment of the prongs in which they are each shaped to form a point.

FIG. 4D is a view of the bone at the alveolar ridge, showing the perforations resulting from use of the tips of FIG. 3C.

FIG. 6 is an Osteotome of the present invention, formed with the single port tip of FIG. 4 being releasably received by the handle and support member of FIG. 1, and with the port being coupled to the outlet of a syringe using a tube.

FIG. 6A is an end view of the exit orifice in the top surface of the tip in FIG. 6.

FIG. 6B is an end view of a first alternate embodiment of the top surface of the tip in FIG. 6, illustrating use of a plurality of exit orifices.

FIG. 6C is an end view of a second alternate embodiment of the top surface of the tip in FIG. 6, illustrating use of a cruciform-shaped exit orifice.

FIG. 6D is an end view of a third alternate embodiment of the top surface of the tip in FIG. 6, illustrating use of a hexaform-shaped exit orifice.

FIG. 18 illustrates an Osteotome formed to releasably receive a series of tips within a barrel portion of the support member so as to protrude beyond a distal end of the support member, and with the support member also having first and second ports being in fluid communication with a conduit within the barrel portion.

FIG. 18A illustrates the barrel portion of the support member of FIG. 18 and caps that may be used to plug the first and second ports, and further illustrates a series of tips that may be received within the barrel portion for use during a sinus lift procedure.

FIG. 19 illustrates the Osteotome of FIG. 18 being received within the bone of the alveolar ridge, and with a first tip of the series of tips being received within the barrel portion to be used to cause up-fracturing of the cortical layer.

FIG. 19A is an exploded view of the barrel portion of the Osteotome of FIG. 18 and of the tip of FIG. 19.

FIG. 19B illustrates the Osteotome of FIG. 18 being received within the bone of the alveolar ridge, and with a second tip of the series of tips being received within the barrel portion to be used to cause cutting of the cortical layer.

FIG. 19C is an exploded view showing the barrel portion of the Osteotome of FIG. 18 and of the piezotome tip shown in FIG. 19B.

FIG. 21 illustrates the Osteotome of FIG. 18 being received within the bone of the alveolar ridge, and with a fourth tip of the series of tips being received within the barrel portion to be used to deliver bone fragments using an integral syringe-adapter and a syringe connected thereto.

FIG. 21A is an exploded view of the barrel portion of the Osteotome of FIG. 21 and of the tip shown in FIG. 21.

DETAILED DESCRIPTION OF THE INVENTION

Figure 1A:
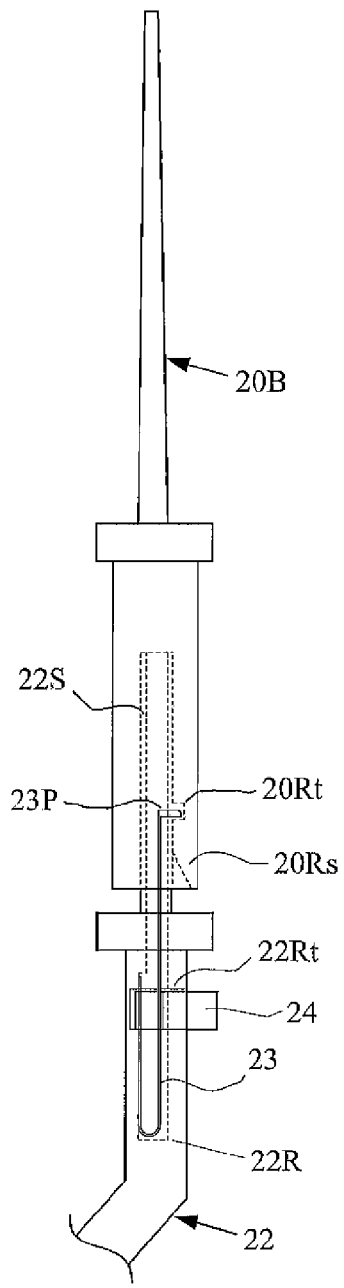
FIG. 1A illustrates an enlarged detail view of the replaceable tip and the means for releasably receiving the tip by the handle of the present invention.
Figure 1:
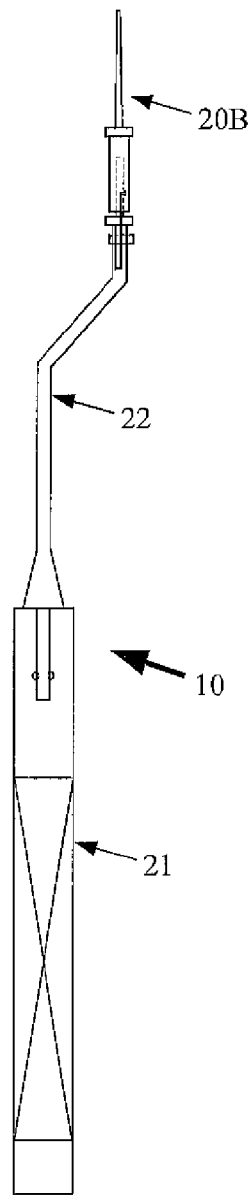
FIG. 1 is a side view of an Osteotome of the present invention, having an offset handle and support member arrangement that is adapted to receive a replaceable tip comprising a conical tip, for use in causing bone compression of the maxilla at the implant site.

FIG. 1 shows a multi-functional Osteotome of the present invention being configured with a tip that is usable for providing the necessary expansion and compaction of bone surrounding an implant pilot hole in an alveolar ridge, during a Sinus Lift procedure. One aspect of the multi-functional Osteotome disclosed herein is that it may comprise a series of replaceable tips that may be releasably received onto a handle/support member, to eliminate the need for procuring multiple sets of handles with various different integral tips. Each of these various tips may be particularly adapted to perform different functions during the sinus lift procedure, and each may be releasably received upon the support member of the handle at a particular point in the surgery, when the corresponding function must be accomplished.

The different tips may be releasably received upon the handle using one of several different structural arrangements. In a basic arrangement, each of the tips may comprise threading that permits it to be threadably received on a threaded portion of the handle. The tip may comprise internal threading that may be engaged by corresponding external threading on a shaft of the handle, or the tip may comprise external threading that may engage internal threading within a recess in a portion of the handle. The threading can be single lead or double lead threading, etc., for external to internal thread interaction.

Figure 3A:
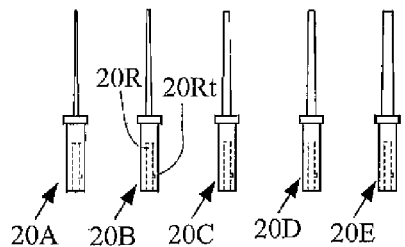
FIG. 3A illustrates a series of conical tapered tips that may be releasably secured to the handle member of the present invention, and may be successively used for the gradual diameter escalation in causing bone compression of the maxilla at the implant site.

To provide for an easier and quicker mounting arrangement for the interchangeable mounting of the tips upon the handle of the Osteotome, the push-button quick-release used for a socket wrench may be utilized. The quick release arrangement shown by U.S. Pat. No. 3,924,493 to Penner, the disclosures of which are incorporated herein by reference, is adapted for use with the present invention, and is illustrated within the enlarged detail view of FIG. 1A. A support member 22, which may be releasably secured to the handle member 21, as seen in FIG. 1 and described in the Applicant's aforementioned co-pending patent application, may have a shaft 22S that is received within a corresponding recess 20R in each of the tips. The recess may be cylindrical, in which case anti-rotation of the Osteotome tip 20B may be provided by the prong 23P of the U-shaped spring 23 that is disposed within a recess 22R in the support member 22. The prong 23P of the U-shaped spring 23 may extend transverse to the centerline of the shaft 22S out of an opening therein, to be received within a recess 20Rt that extends transverse from recess 20R. Rather than relying upon the prong 23P for anti-rotation of the tip 23B, the recess 20R in the Osteotome tips may each have a keyed cross-sectional shape, such as the D-shaped cross-section shown in the bottom view of FIG. 3B, which may receive a shaft 22S of the support member 22 that may have a corresponding D-shaped cross-section.

A button 24 may be slidably received in a recess 22Rt that extends transverse to recess 22R in the support member 22. The spring member 23 may be received into the recess 22R and through an opening in the button 24, whereby depressing of the portion of the button that is protruding out from the side of the support member, causes deflection of the side of the U-shaped spring with the prong 23P, causing the prong to be withdrawn from the recess 20Rt in the Osteotome tip 20B, permitting removal of the tip. Securing of the tip 20B upon the shaft 228 of the support member 22 may occur in the reverse manner—by aligning of the D-shaped recess 20R of the tip with the D-shaped cross-section of the shaft of the support member, and advancing of the Osteotome tip upon the shaft, with the button initially depressed to allow entry of the prong within the recess of the tip. The tip may thus be advanced until the prong 23P springs outwardly into the transverse recess 20Rt of the tip.

The requirement of depressing the button in order to secure the tip 20B upon the shaft 228 of the support member 22 may be eliminated, by having a sloped portion 20Rs for recess 20R at the end of the tip, as seen in FIG. 1A. The sloped wall forming the recess portion 20Rs may thereby cause deflection of the prong 23P of the leg of the U-shaped spring 23, as the tip is slid onto the shaft, once the end of the prong contacts the sloped wall, thereby causing deflection of the spring. The end of the prong 23P may be appropriately chamfered to provide for better initial contact between the prong and the wall forming the sloped portion 20Rs for recess 20R.

Figure 2:
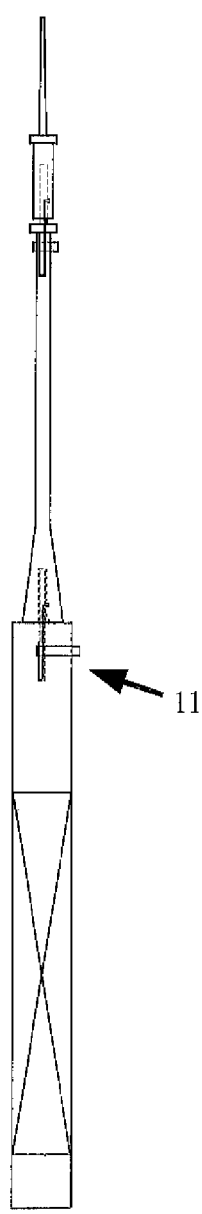
FIG. 2 is a side view of an Osteotome of the present invention, having a handle with a straight support member that is adapted to receive a replaceable tip comprising a conical tip, for use in causing bone compression of the maxilla at the implant site.

In addition to adapting the quick release arrangement shown by U.S. Pat. No. 3,924,493 to Penner for securing the Osteotome tips, as discussed above, the quick release arrangement shown by U.S. Pat. No. 4,508,005 to Herman, the disclosures of which are also incorporated herein by reference, may similarly be adapted. Adaptation of the Herman release mechanism for use herein would result in a release button being located proximate to the bend in the support member 22, as seen in FIG. 1A. Furthermore, the releasable attachment of the support member 22 to the handle 21 may also be achieved using the same quick release arrangement, as shown in FIG. 2. Lastly, where it may not be desired to be able to interchange the handle portion for one having a different size, the support member 22 and handle portion 21 may be formed to be a single piece handle member.

Figure 1C:
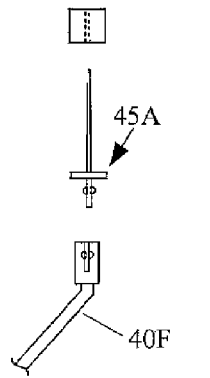
FIG. 1C is an exploded detail view of the component parts of the Osteotome of FIG. 1B.
Figures 1B, 1D:
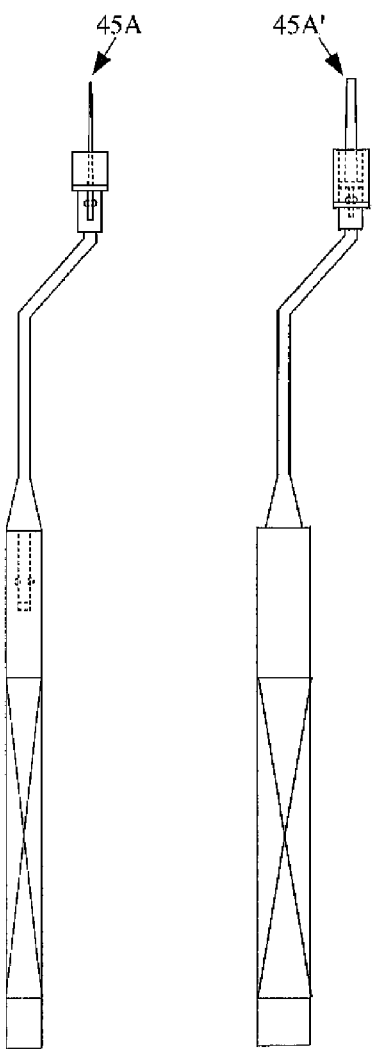
FIG. 1B illustrates an offset handle, a support member, and a replaceable tip being received within the support member, and with a reduction cylinder, for limiting the depth of penetration, being received upon the tip.
FIG. 1D illustrates an offset handle, a support member, and a replaceable tip being received within the support member, and with a reduction cylinder, for limiting the depth of penetration, being received upon the support member.
Figure 1E:
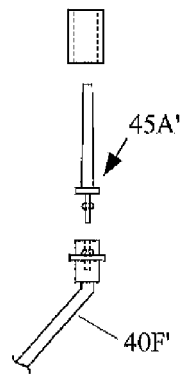
FIG. 1E is an exploded detail view of the component parts of the Osteotome of FIG. 1D.

FIG. 1B illustrates the Osteotome arrangement from FIG. 4E of the Applicant's above-mentioned co-pending application, but with use of one of the Applicant's reduction cylinders thereon, where the annular flange that is integral to, and protruding out from, the tip 45E, thereby serves to support the cylinder. FIG. 1D illustrates the same Osteotome arrangement, but where the annular flange for supporting the reduction cylinder is instead integral to, and protruding out from, the support member 40F'. The component parts for the two different arrangements of FIG. 1B and FIG. 1D herein, are shown within FIGS. 1C and 1E.

Figure 3C:
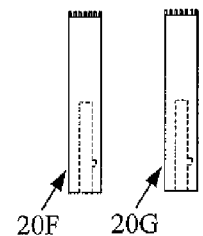
FIG. 3C illustrates a series of tips with various shaped prongs having a specific length to be used to perforate the cortical floor prior to up-fracturing.
Figure 3B:
FIG. 3B is a bottom view of one embodiment of the cross-section for the replaceable tips that may be releasably received by the handle of the present invention.

The Osteotome tips 20F and 20G, seen in FIG. 3C, are adapted for preparing the cortical bone layer of the alveolar ridge to undergo the up-fracturing process in accordance with the present invention. Use of one of those tips is illustrated in FIG. 4, where it is releasably received by the support member 22. A top view of the tip is seen in FIG. 4A, while two section cuts through the tip (FIGS. 4B and 4C) show two of the possible embodiments for the prongs that may be used. In FIG. 4B, the prongs $20F_P$ may each have the upper-most surface be angled so as to form a sharp point at the end to the prong. The pointed end would enable easier piercing of the remaining cortical layer, as described hereinafter. In FIG. 4C, the prongs 20Gp may each have the upper-most surface be curved so as to form a generally rounded or elliptical end to the prong. Use of the tips 20F and 20G may be as follows. After the pilot hole for the implant axis has been formed to be roughly 1-2 mm short of reaching the sinus floor, and after the conical tips of FIG. 3A have been used for compression of the bone and expansion of the opening, one of the tips 20F and 20G may be used in the implant socket, with a force being exerted thereon to cause perforations within the remaining 1-2 mm of the cortical layer, as seen in FIG. 4D. Therefore, the length of the prongs may be approximately 1-2 millimeters, to cause perforations of the cortical layer through most, if not all of, the remaining distance to the sinus membrane. The length of the prongs should not be any longer than 1-2 mm, so as to prevent the prongs from impinging excessively upon the bottom of the sinus membrane. Use of the rounded tip of prongs 20Gp may better serve to reduce or eliminate agitation of the sinus membrane if contacted by this perforating tip, and may also require less exacting control in coordinating the length of the prongs with the remaining 1-2 mm of depth of the cortical layer.

Figure 3D:
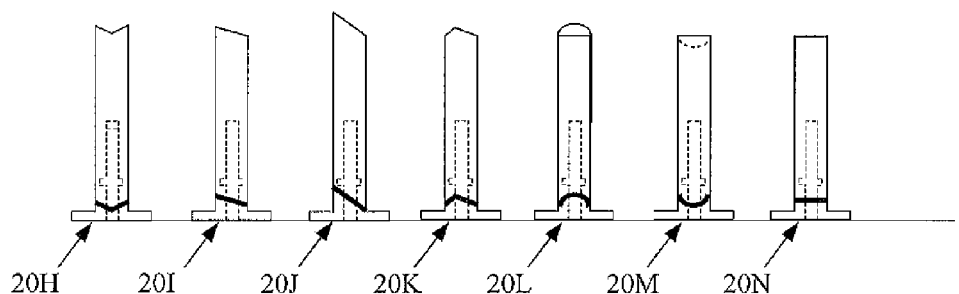
FIG. 3D illustrates a series of tips with various shaped ends that may be used for up-fracturing of the cortical layer at different locations.
Figure 5:
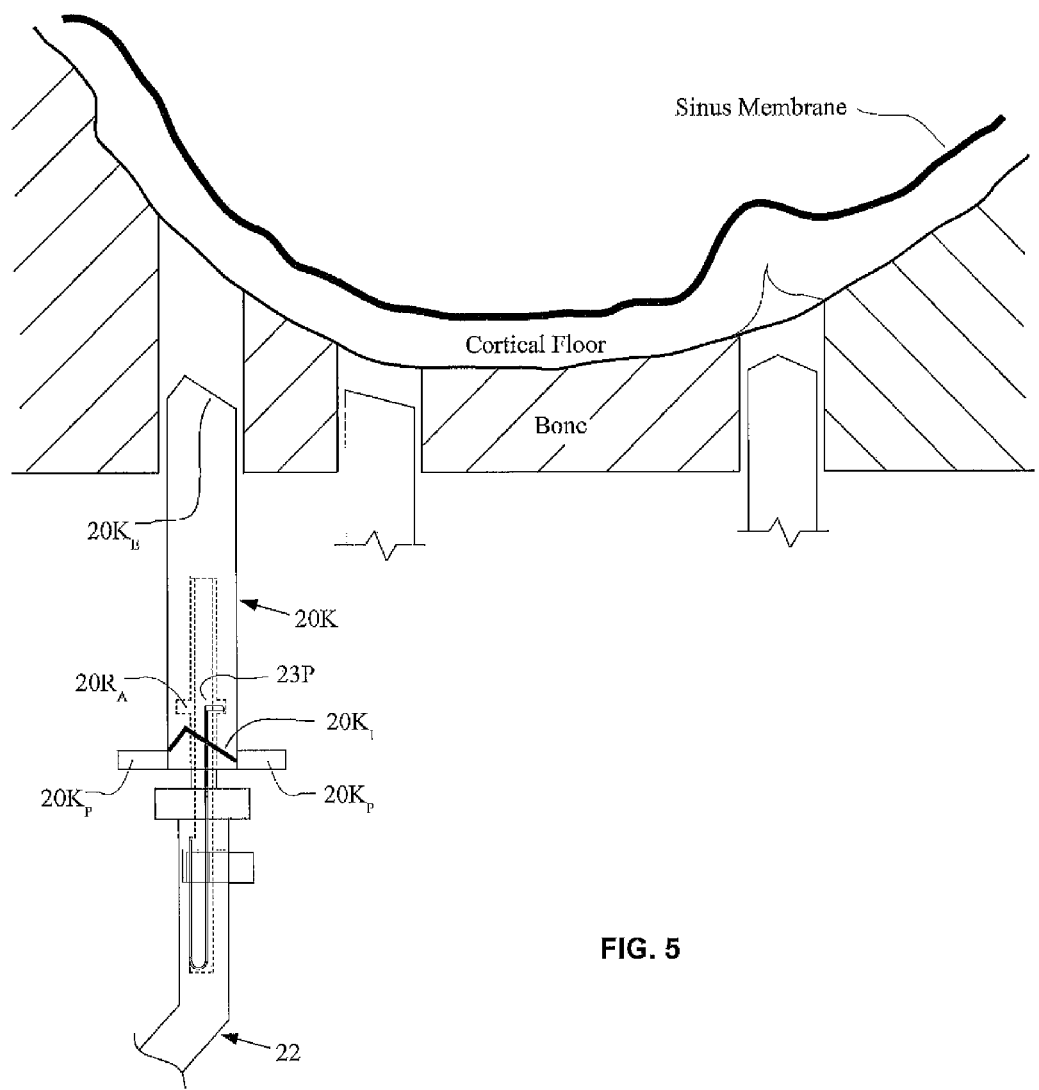
FIG. 5 is a view illustrating use of several of the tips of FIG. 3D tips being used for up-fracturing of the cortical layer at respective locations.

The Osteotome tips 20H, 20I, 20J, and 20K, seen in FIG. 3D, are adapted for the up-fracturing process in accordance with the present invention. Use of several of those tips is illustrated in FIG. 5, where one of the tips is shown releasably received by the support member 22. Each of the tips may have an end surface that is shaped—possibly with compound contouring or possibly just being angled or with multiple angled surfaces- to more closely match and contact the surface area of the contoured shape of the cortical layer within the implant socket. (Note that the end surface for these tips, or any of the other tips disclosed by the Applicant, may be convex-shaped as with tip 20L, or concave-shaped as with tip 20, or may be generally flat as with tip 20N, and may serve other functions during the sinus lift procedure, such as packing of the bone particles above the cortical layer but beneath the lifted sinus membrane). When used after perforating the remaining cortical layer using tips 20F/20G, the tips of FIG. 3D may serve to more uniformly up-fracture the remaining cortical layer, instead of using a prior art tool that may appear, from the perspective of the contoured membrane, to be pointed or to have a sharp edge, which may not only pierce the cortical layer but may also inadvertently perforate the sinus membrane, which would require repair before the procedure could continue. (Note that the Osteotome tips 20F and 20G for causing perforations to the remaining cortical layer may therefore also have the prongs protruding from an end surface that may be similarly angled/contoured). In order for the oral surgeon to have a positive indication of the positioning of the contoured end surface $20K_E$ of the tip 20K, so that the contouring may match that of the cortical layer for the particular implant socket, the tip may have a raised indicator $20K_I$ towards the bottom of the tip, and which may be positioned to extend from the side of the tip to match the angles/contouring of the end surface $20K_E$. Also, in order for the oral surgeon to be able to reorient the clocking of the tip 20K to match the contour of the cortical layer, the tip, as seen in FIG. 5, may receive the prong 23P of the U-shaped spring 23 in an annular opening $20R_A$ instead of the transverse recess 20Rt, so that rotation of the tip upon the support member is thereby permitted, and the prong 23P merely serves to prevent inadvertent separation of the tip from the support member. In addition, the tips 20H, 20I, 20J, and 20K may each have a pair of flat protrusions $20K_P$ protruding outwards from a bottom portion, to be usable for easily rotating the tip relative to the support member, to cause the necessary clocking of the end surface $20K_E$ of the tip.

Figure 3E:
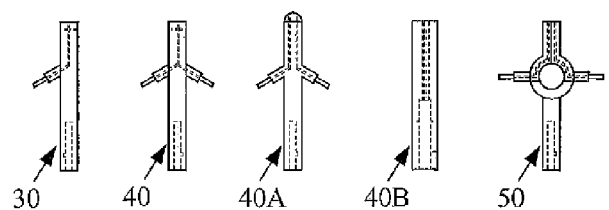
FIG. 3E illustrates a series of tips that may be releasably secured to the handle and support member of the present invention, and may be used for the introduction of air, saline solution, bone putty, or bone gel into the implant site, and for its removal therefrom.
Figure 3F:
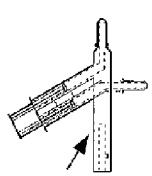
FIG. 3F illustrates a tip with a redundant balloon arrangement that may be releasably secured to the handle and support member of the present invention, and which may be used for elevating of a sinus membrane by the first balloon, and for also providing a visual indication of the extent of deployment of the first balloon by corresponding deployment of a second balloon outside of the sinus cavity.
Figure 3G:
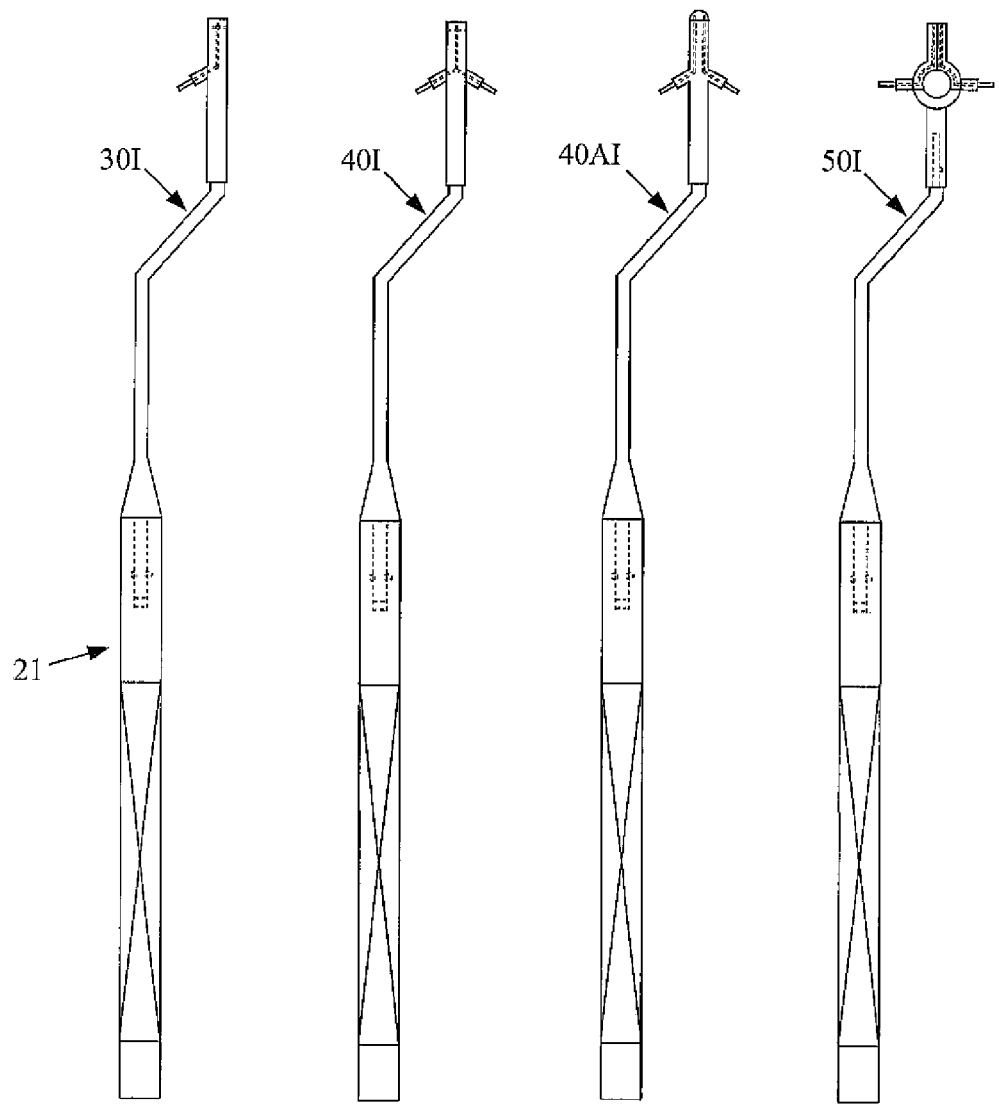
FIG. 3G illustrates a different embodiment of the tips of FIG. 3E, in which each of them are formed integral with a support member.

The Osteotome tips 30, 40, 40A, 40B, and 50, shown in FIG. 3E, are configured for using either air or saline solution for the displacing/lifting of the sinus membrane. As seen for the arrangement 14 in FIG. 6, the introduction of saline solution may be accomplished through the use of a syringe 290 that uses, in place of a needle, a tube 280 to couple its outlet opening with the connector 242 of the port 241 of the tip 30. This arrangement 14 permits the oral surgeon to introduce into the region above the sinus floor and below the sinus membrane, only a particular measured amount of saline solution that is calibrated in accordance with the specific geometry of the patient's physiology (age/jaw dimensions) and the degree to which the practitioner needs to lift the membrane.

Figure 6E:
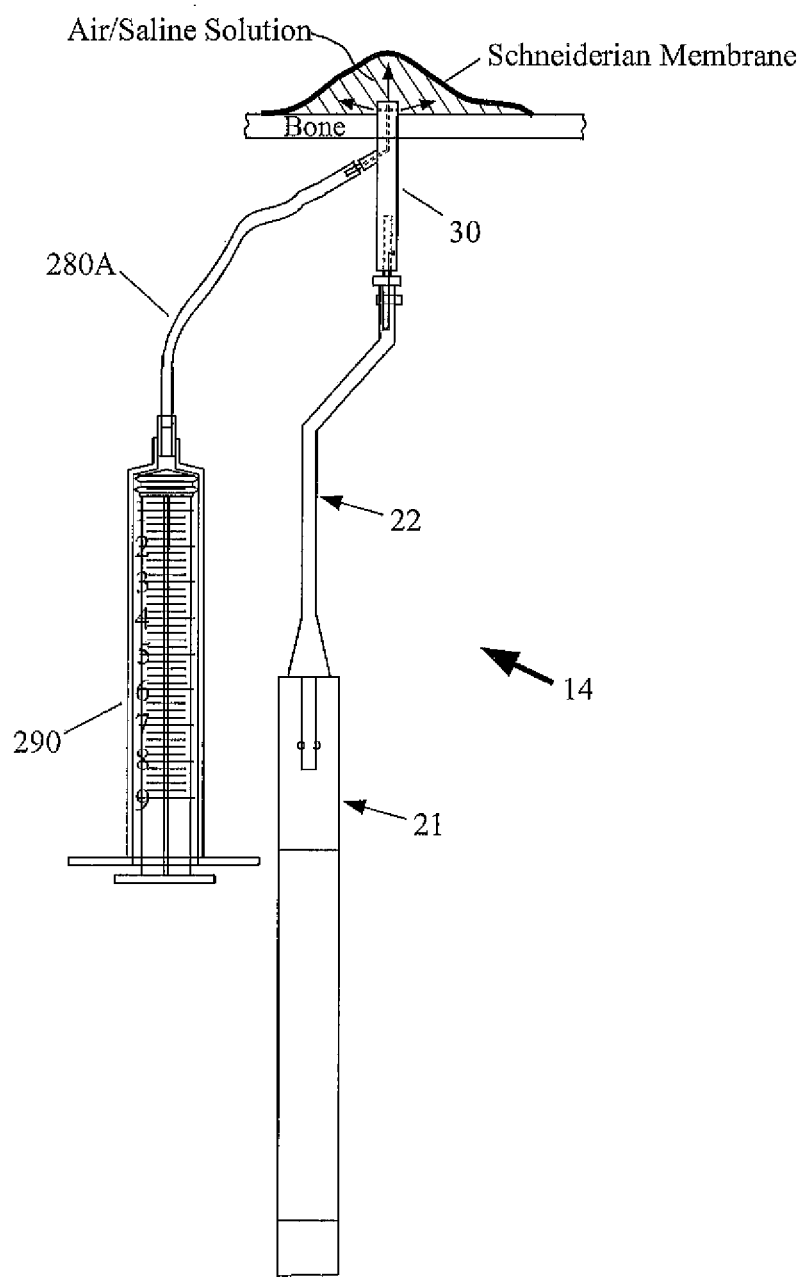
FIG. 6E is the Osteotome arrangement of FIG. 6, with the single port tip having been inserted into the implant socket, and with the syringe having been utilized to expel saline solution from within the tube, to raise the sinus membrane.
Figure 6F:
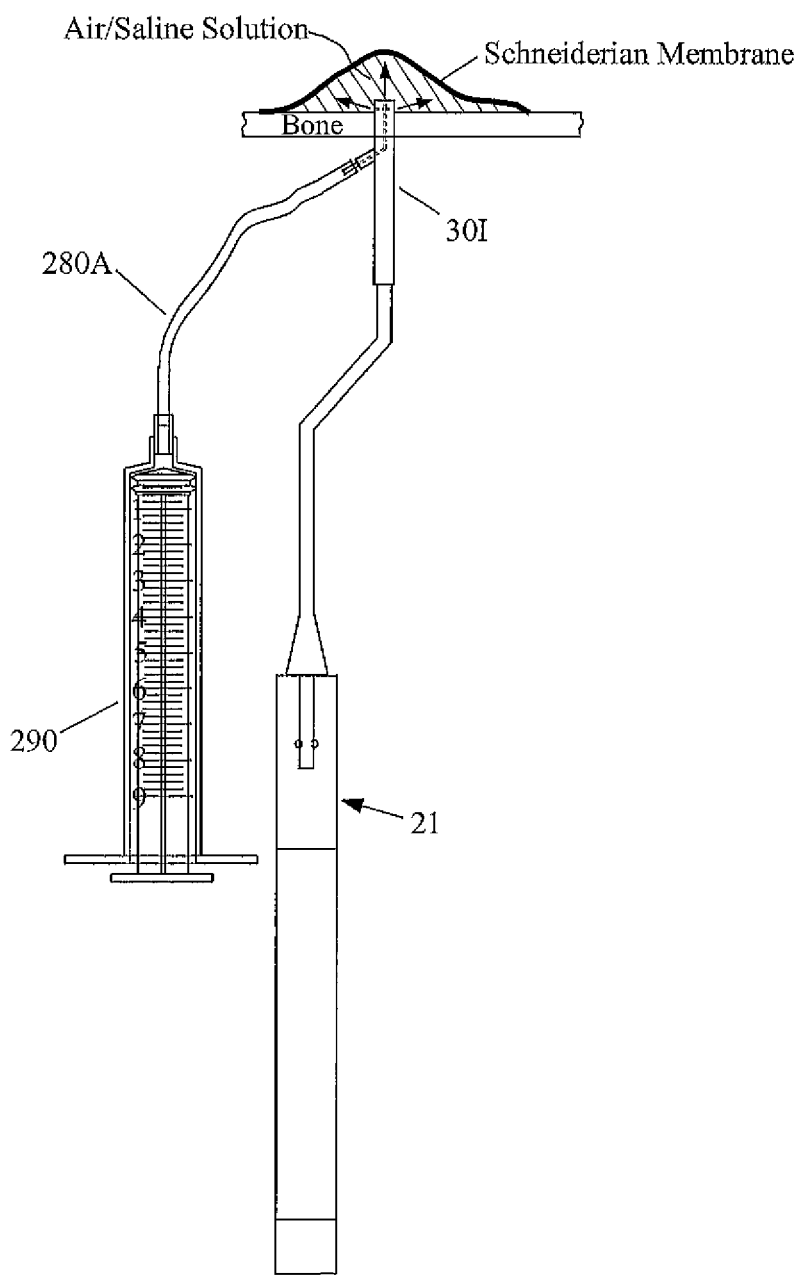
FIG. 6F is the Osteotome arrangement of FIG. 6E, but where the single port tip received upon the support member is replaced by the integral port/support member of FIG. 3G.

To begin the process, the oral surgeon may first draw saline solution into the syringe 290, and then, with the tip of the Osteotome being elevated, he/she may advance the plunger to release excess saline solution out of the exit orifices until only the desired amount of saline solution 299 remains trapped within the syringe for delivery into the maxillary sinus, as indicated by the plunger's position relative to the graduated scale. Saline solution will also remain within the tube 280, as well as the conduit 30C of the tip of the Osteotome. The tip 30 may then be urged into the implant socket using handle 21, to be securely received therein so as to form a fluid-tight interface (FIG. 6E). The plunger of the syringe 290 may then be smoothly advanced to introduce the desired amount of saline solution above the sinus floor to cause the requisite separation of the membrane from the cortical floor.

The exit orifices of tip 30 may be as seen in FIG. 6A, where there is a single orifice in the top surface of the tip, and optional side orifices. Note that the top surface may actually be rounded rather than being flat, so as to not impose a sharp edge against the sinus membrane. Instead of the single orifice in the top surface of the tip (FIG. 6A), there may be a plurality of orifices, as seen in FIG. 6B, or there may be a patterned opening, as seen for the cruciform-shaped opening in FIG. 6C, and the hexaform-shaped opening of FIG. 6D, and as discussed in the aforementioned co-pending application.

Figure 7:
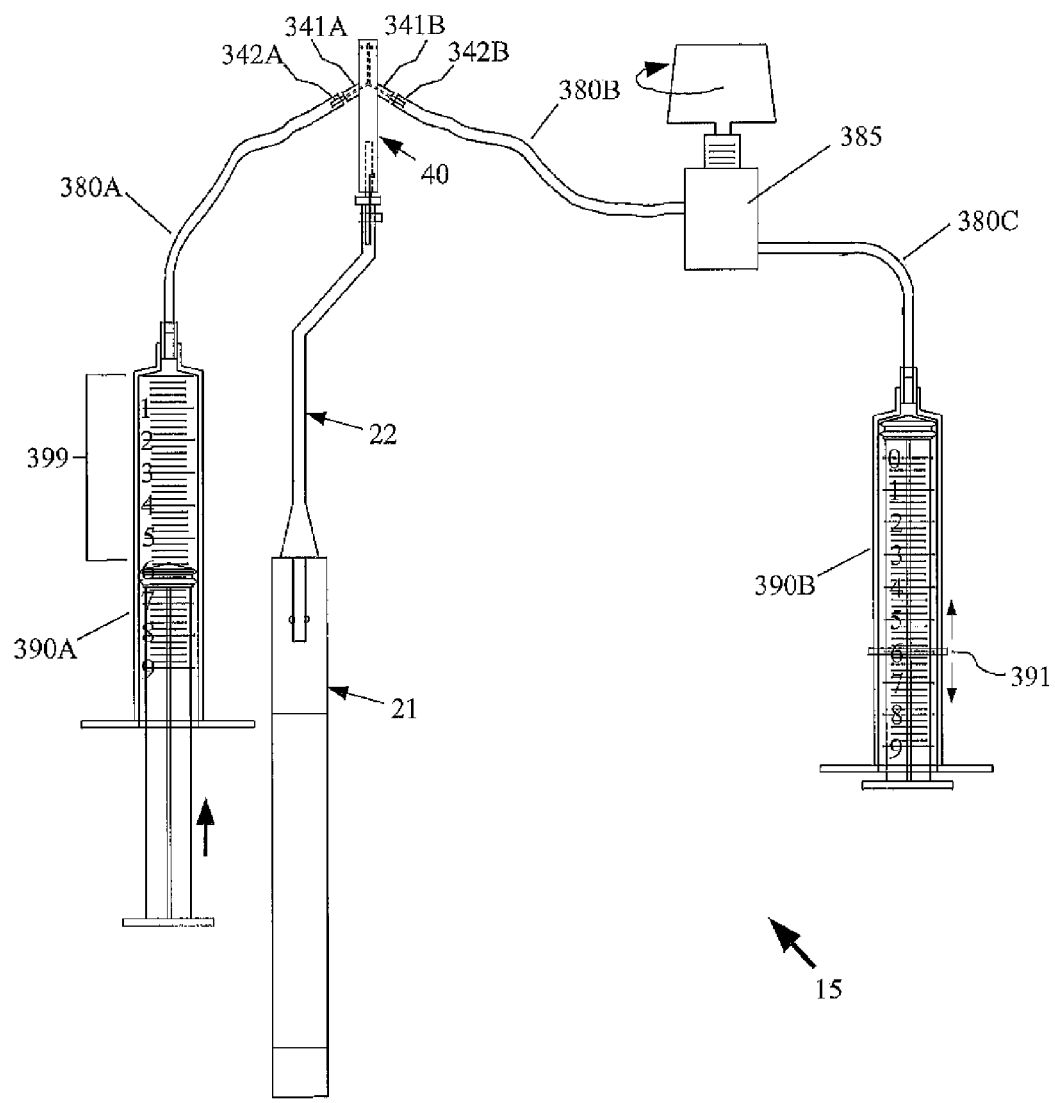
FIG. 7 is an Osteotome formed with the dual port tip of FIG. 4 being releasably received by the handle and support member of FIG. 1, and with the first port being coupled to the outlet of a first syringe using a tube, and with the second port being coupled to a second syringe with a valve therebetween.

A further embodiment of the Osteotome of the present invention is shown by the arrangement 15 of FIG. 7. To better inform the oral surgeon that the sinus membrane has not been perforated as a result of the elevating of the membrane, a perforation which may result in the drainage of a distinct or indistinct portion of the saline solution from the maxillary sinus into the middle meatus of the nose, the arrangement 15 may accomplish lifting while simultaneously providing for both the measured delivery of saline solution and the measured evacuation of the saline solution therefrom. The Osteotome arrangement 15 may utilize tip 40, which may have its first port 341A of first connector 342A receive a first tube 380A, that is coupled to the outlet opening of syringe 390A. The second port 341B of second connector 342B of tip 40 may receive a second tube 380B that is coupled to an inlet of a valve 385. Another tube 380C may couple the outlet of the valve 385 to the outlet of a second syringe 390S.

The Osteotome arrangement 15 may be utilized to introduce a measured amount of saline solution to cause lifting of the sinus membrane, and to thereafter measure the saline solution evacuated from the maxillary sinus to verify that the membrane has not been perforated. The valve 385 should initially be closed, by being rotated as shown. Next, the saline solution may be introduced into the Osteotome arrangement 15 (into tube 380B and tube 380A, by drawing the solution into syringe 390A) to be proximate to the top of the tip 40 of the Osteotome. With the valve being closed, the tube 380B would be filled with saline solution, but tube 380C would remain empty. If there is any difficulty in receiving saline solution within tube 380B, as the intake suction from syringe 390A may limit its tendency towards traveling down the port 341B on the opposite side of the tip, the valve 385 may initially be opened and the plunger of syringe 390B may be withdrawn to draw the solution into both tubes 380B and 380C. Thereafter, the valve 345 may be closed, the connection of tube 380C to the valve 345 may be loosened to permit the solution to flow out from tube 380C and out from syringe 390B, after which tube 380C may be reconnected to valve 345.

Figure 7A:
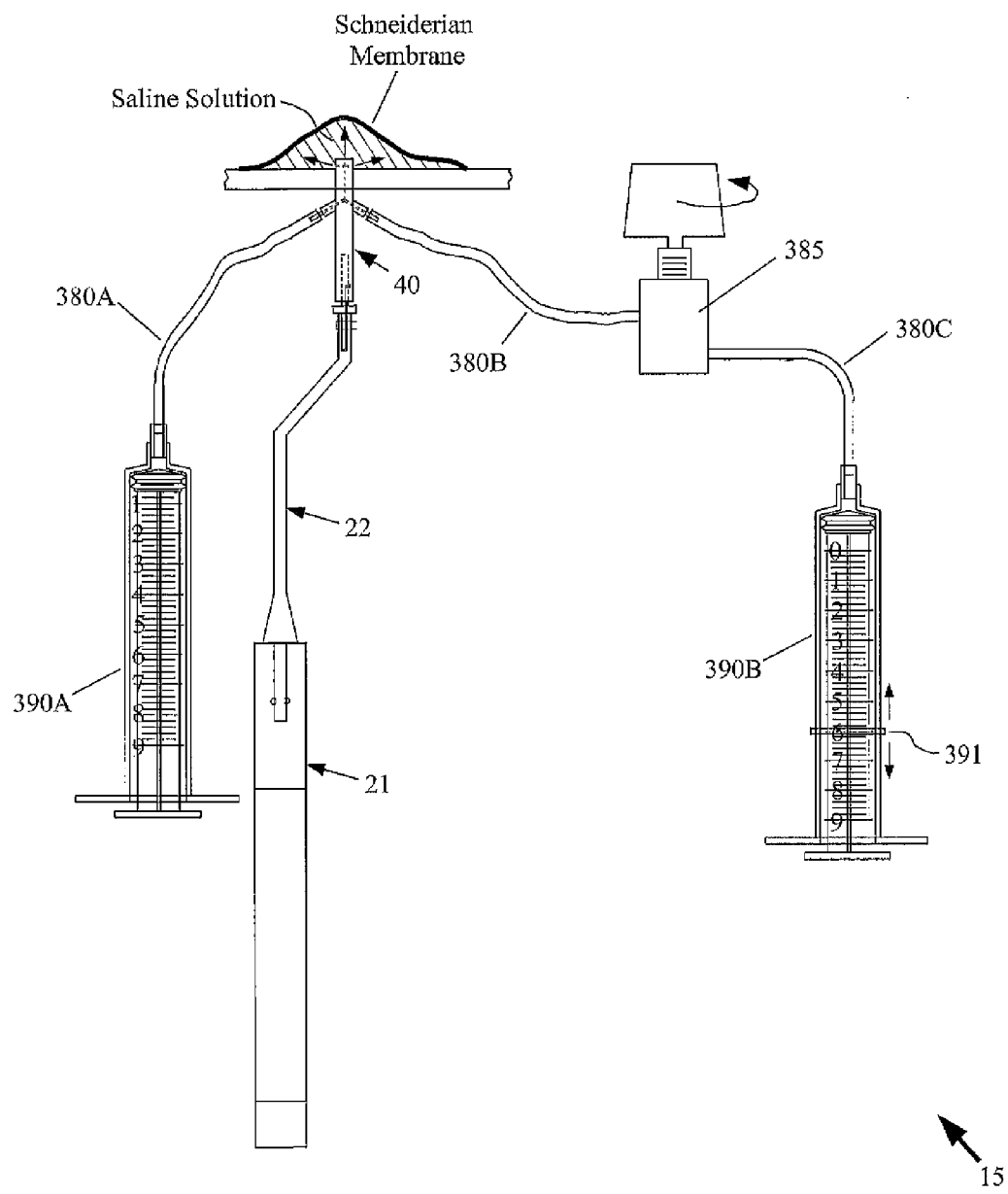
FIG. 7A is the Osteotome arrangement of FIG. 7, with the dual port tip having been inserted into the implant socket, and with the syringe coupled to the first port having been utilized to expel saline solution from within the tube, to raise the sinus membrane.

To utilize the Osteotome arrangement 15, the oral surgeon may urge the tip 40 into the implant socket, as illustrated in FIG. 7A, by using handle 21, so that the tip may be securely received therein to form a fluid-tight interface. To create the fluid-tight interface, the diameter of the tip 40 may be sized to be slightly smaller than the largest diameter of the last conical bone-compressing tip (20A-20E) that was used to for forming the finished socket.

Figure 7B:
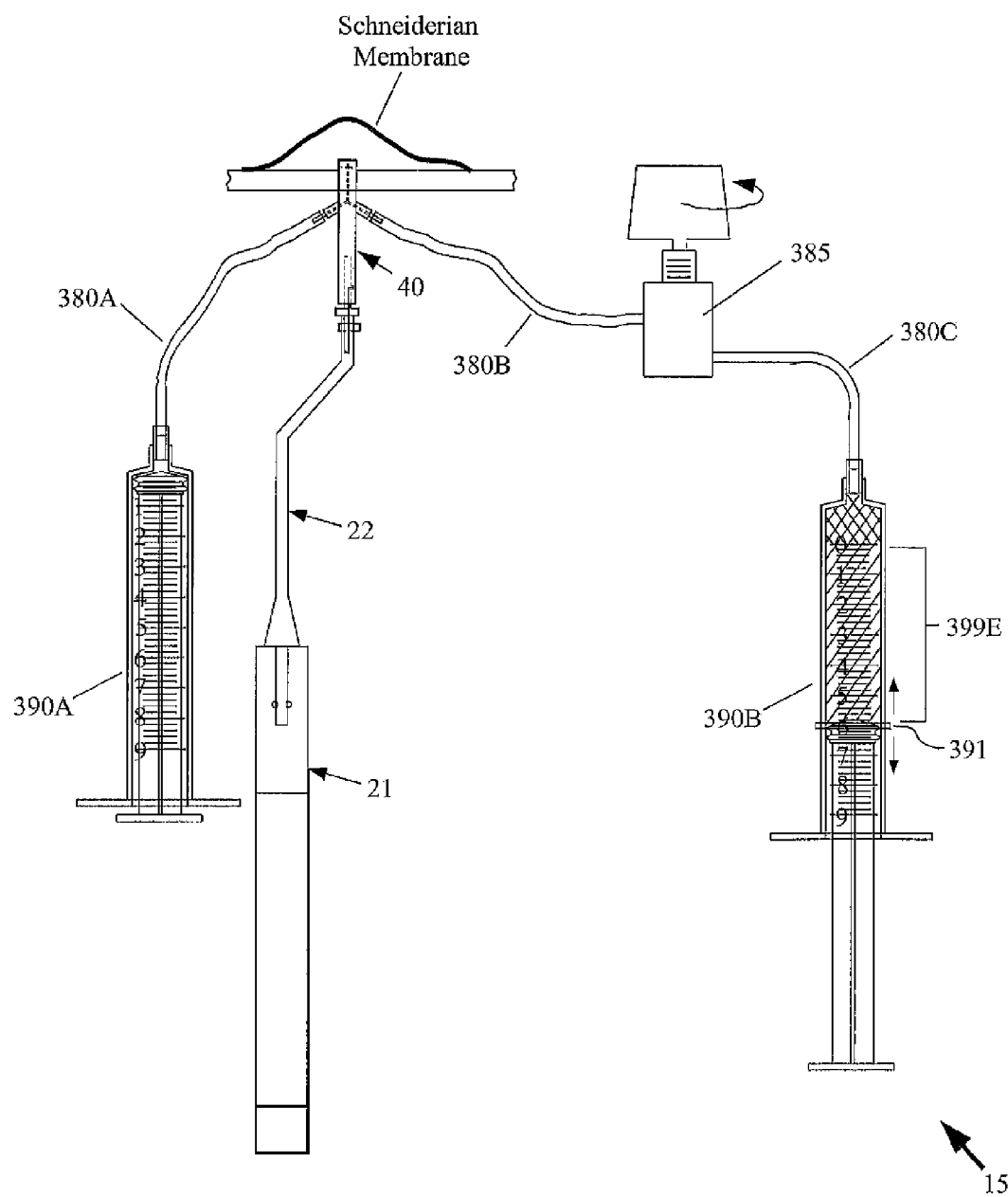
FIG. 7B is the Osteotome arrangement of FIG. 7A, after the valve has been opened and the plunger of the second syringe has been withdrawn to evacuate the saline solution from the sinus cavity to be measured therein.

The plunger of the syringe 390A may then be smoothly advanced to introduce the desired/measured amount of solution 399 above the sinus floor, to cause the requisite separation and lifting of the membrane. With the syringe 390A being maintained in the depressed position that caused expulsion of the saline solution from its tube, as seen in FIG. 7A, and with the Schneiderian membrane having thus been lifted, as illustrated therein, the valve 385 may then be opened, and the plunger of syringe 390B may withdrawn to evacuate the saline solution from above the patient's sinus floor, as seen in FIG. 7B. If no significant quantity of the measured amount of saline solution has been lost, such as through a perforated membrane, the evacuated saline solution 399E received between the graduated marks of syringe 390B should approximately match the original amount of saline solution 399 that had been expelled from syringe 390A.

Note that the numbering for the graduated marks of syringe 390B do not begin at the top of its tube, as the fluid volume corresponding to this displacement (the cross-hatched area) may be calibrated to account for the amount of saline solution that had initially been contained within tube 380B and the amount that had initially occupied the vertical conduit above its juncture with the angled conduits of ports 341A and 341B (see FIG. 7). Thus, the amount of saline solution actually evacuated from above the sinus floor would be measured downward beginning with the graduated marking labeled as zero (the single hatched area), and with the plunger set so that the top fluid level is positioned at an upper graduated mark, which may be at the end of the tube 380C within the outlet of the syringe 390B. If the sinus membrane had been punctured, the amount of saline solution evacuated and now contained within syringe 390B would be measurably less than the 6 ml.

To further assist the oral surgeon, as to the expected amount of saline to be evacuated from above the sinus floor, the syringe 390B, as seen in FIGS. 7, 7A, and 7B, may comprise a colored ring 391 that may be slidably received upon the tube of the syringe. When the oral surgeon has determined the amount of saline solution needed for raising of the sinus membrane, and has drawn it into syringe 390A, e.g., 6 ml for the syringe 390A in FIG. 7, the surgeon may then slide the ring 391 on syringe 390B to the 6 ml graduate mark as a visual reminder of the amount of saline solution expected from the subsequent evacuation. Alternatively, the syringe 390A may have the ring 391 be slidably mounted thereon, which may be moved to the location indicating the amount of saline solution that will be introduced above the patient's sinus floor using that syringe. The surgeon may thereafter perform the evacuation of saline solution into syringe 390B, and then compare the amount of saline therein with the position of ring 391 on syringe 390A. Alternatively, a ring 391 could be used on both syringe 390A and syringe 390B.

It should be noted that other arrangements for the initial and final saline solution levels may be utilized. For example, initially, there need not be any fluid in tube 380B, so that no shill in the graduated markings would be necessary for syringe 390B. However, in order to prevent entry of saline solution therein during its expulsion from syringe 390A, which is intended for lifting the sinus membrane, a means of preventing fluid from entering therein would be necessary. Rather than adding another flow control valve at that location, the functionality of valve 385 in such an arrangement may be incorporated directly into the tip 40. During lifting of the membrane, the valve may block flow towards syringe 390B, and during evacuation, the valve would only permit flow towards syringe 390B and prevent backflow towards tube 380A and syringe 390A.

Figure 7C:
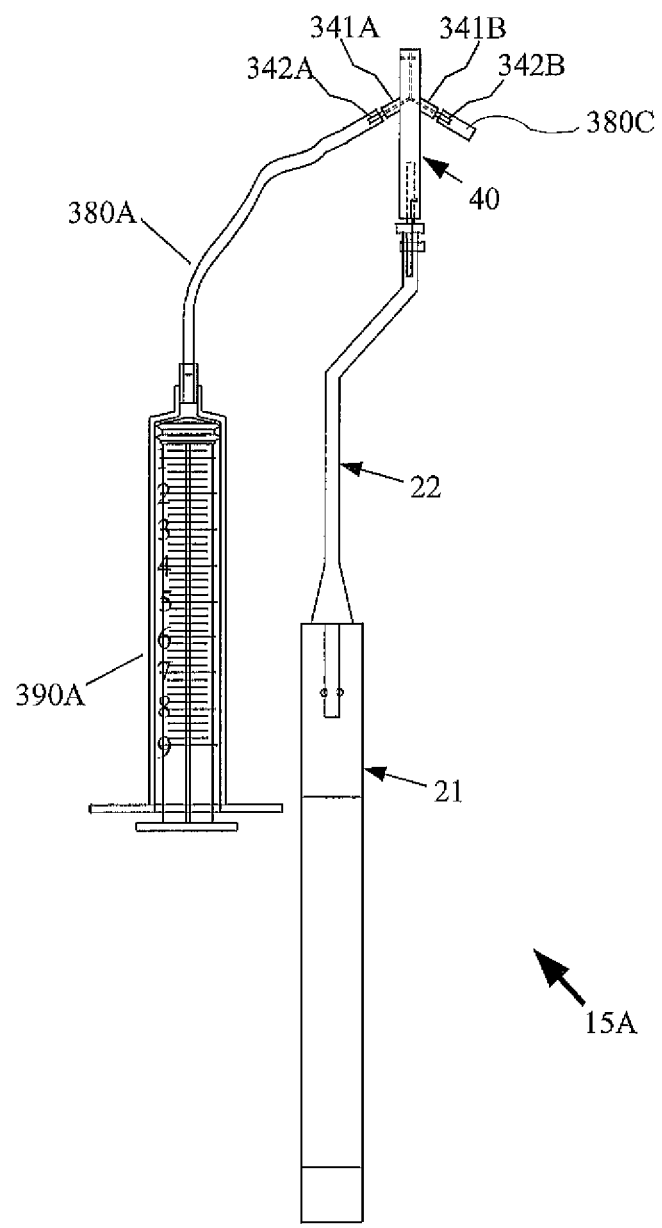
FIG. 7C is an Osteotome formed with the dual port tip of FIG. 4 being releasably received by the handle and support member of FIG. 1, and with the first port being coupled to the outlet of a first syringe using a tube, and with the second port being plugged by a cap being threadably received thereon.
Figure 7D:
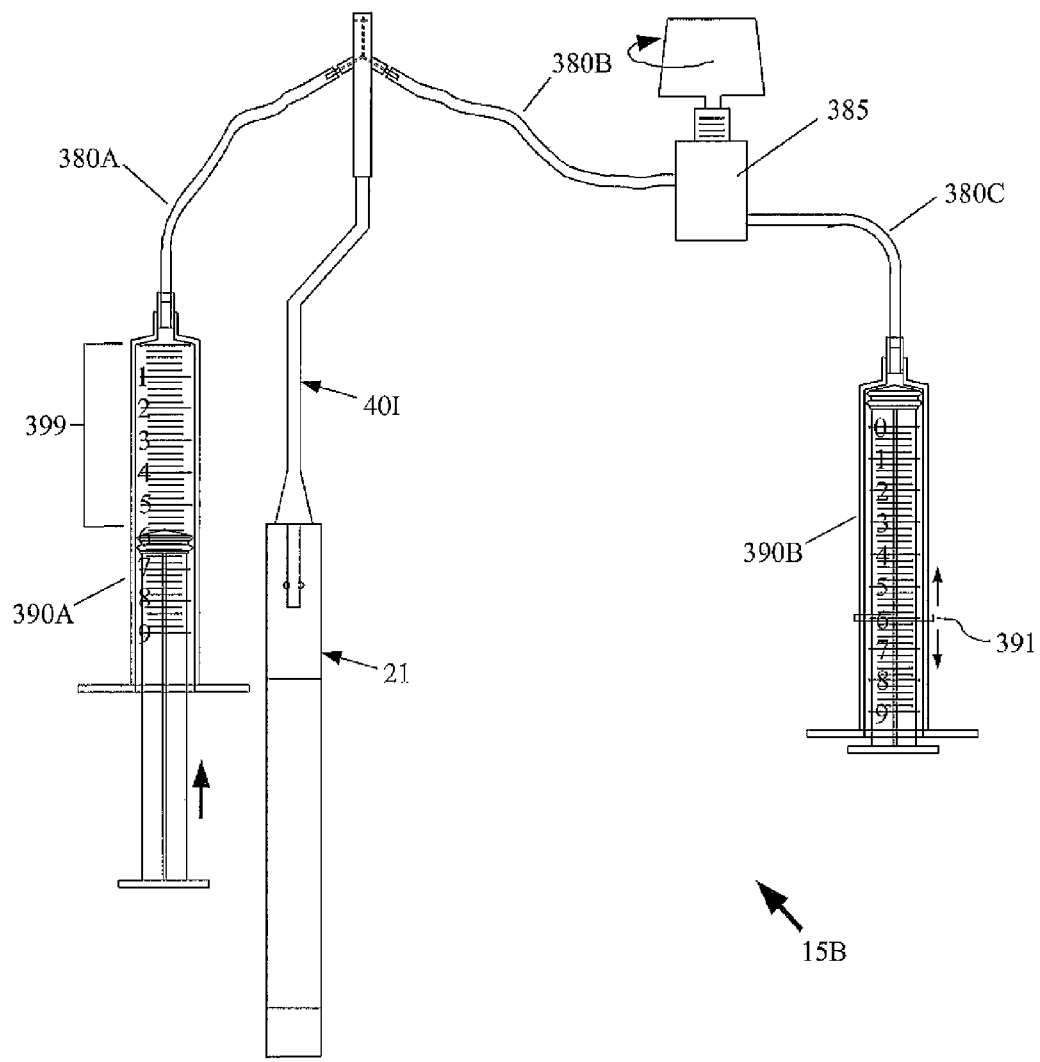
FIG. 7D is the Osteotome arrangement of FIG. 7, but where the double port tip received upon the support member is replaced by the integral port/support member of FIG. 3G

A further use of the tip 40 of Osteotome arrangement 15 is shown by the arrangement 15A in FIG. 7C. The second connector 342B of the second port 341B may be threaded, to be able to threadably receive a cap member 380C, instead of the tube 380B. The ability to apply the cap 380C onto the second connector 342B to seal the second port 341B may permit the oral surgeon, after having performed sinus elevation using saline solution that has been evacuated per the above discussion, to thereafter utilize the Osteotome to carry air into the implant socket. Threading being added to the first connector 342A of the first port 341A is another possibility that may permit additional functionality.

Figure 8:
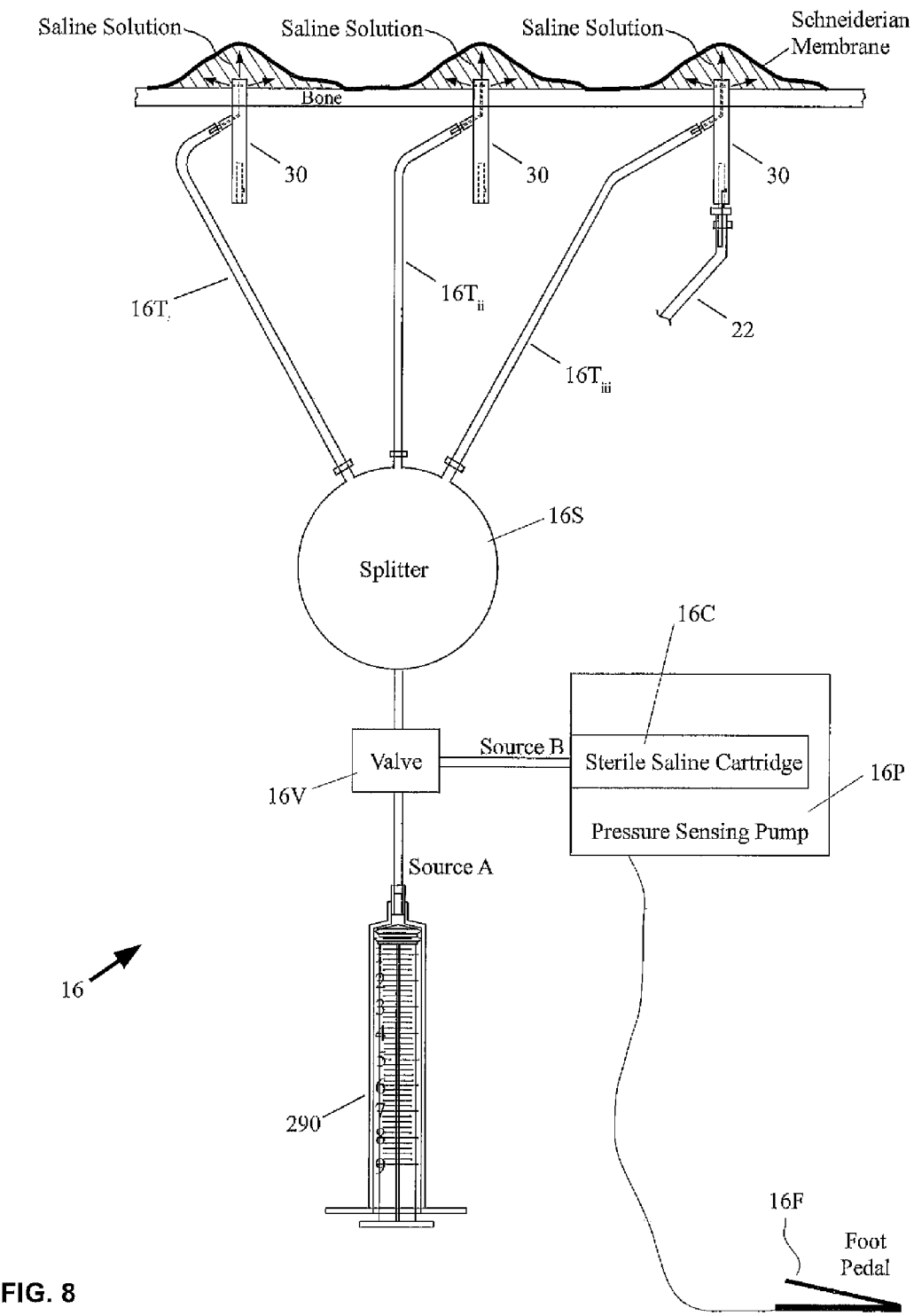
FIG. 8 is an embodiment of the current invention that may utilize several of the tips of the present invention to introduce a measured amount of saline solution at multiple locations to cause lifting of the sinus membrane at those locations, using a carefully regulated flow rate to prevent over-pressurization, with saline solution being supplied from either a first source, being a syringe, or from a second source, being a pressure sensing pump of the present invention.

The Osteotome arrangement 16 in FIG. 8 may also be utilized to introduce a measured amount of saline solution to cause lifting of the sinus membrane, and may do so at multiple locations, and with a very carefully regulated flow rate, so as to prevent over-pressurization from causing a tear in the membrane. As seen in FIG. 8, an Osteotome of the present invention may be used to secure one or more of the tips of the present invention (tip 30 in this example) within one or more implant sockets. The handle portion 21 and support member 22 may be removed from the tips 30 during elevation of the sinus membrane. One or more sources of saline solution (Source A and Source B in this example) may be used to provide saline solution for lifting of the membrane. Each of the sources of saline solution may be in fluid communication with the inlet(s) of a valve 16V, that may be used to port the solution to the tips 30, from either or both of the sources. The outlet of the valve 16V may be in fluid communication, via a tube, with a splitter 16S, which may serve as a reservoir for the saline solution. The splitter 16S may thereby simultaneously deliver saline solution using tubes 16Ti, 16Tii, and 16Tiii, to each of the tips 30 being utilized within a respective implant socket. It should be noted that the valve may be eliminated by having any one of the sources of saline solution coupled directly with the splitter 16S.

Where the saline solution is delivered by the first source, being the syringe 290, the flow rate of saline from the syringe may be roughly controlled by the oral surgeon administering the syringe, through the amount of pressure being applied to its plunger. However, the sensitivity of the oral surgeon, as to the total pressure necessary to cause lifting of the membrane, may not be sufficient in all cases to prevent inadvertently creating an overpressure situation that results in a tear to the membrane. Therefore, the first syringe 290 may be used only for back-up delivery of saline solution, while the primary source of saline solution in this embodiment may be from a second source that may be a pressure sensing pump 16P that may be in accordance with U.S. Pat. No. 5,295,967 to Rhondelet for "Syringe Pump having Continuous Pressure Monitoring and Display", U.S. Pat. No. 5,080,653 to Voss for "Infusion Pump with Dual Position Syringe Locator," and/or U.S. Pat. No. 4,731,058 to Doan for "Drug Delivery System," with the disclosures of each being incorporated herein by reference. In addition, the pressure sensing pump 16P herein may be adapted to receive a sterile saline cartridge 16C, with the pump forcing the saline from the cartridge into the tube connected to the valve 16V, thus the pump may be configured as a peristaltic pump to force saline from the cartridge by applying pressure to the exterior of the cartridge. The pressure sensing pump 16P may thus be used to regulate the flow of saline from the disposable cartridge through the valve 16V, into the splitter 16S, and through the tip 30 to cause elevation of the sinus membrane. The controls on the pump may permit selection of pump sensitivity for pumping to one, or two, or even more tips, for elevation of the sinus membrane at a corresponding number of locations. If the pump's microprocessor and circuitry determines that an excessive amount of pressure is necessary to continue the flow rate of saline, the microprocessor may cause the pump to temporarily halt the pumping of saline, and signal, using an LED or audio alarm, that such pumping has been interrupted. The microprocessor may be able to sense the force required for pumping at one tip to raise the membrane at one location, or the force necessary for two tips to raise the membrane at two locations, etc., and where the total force exceeds the expected force required or where a sudden increase in force must be exerted to maintain a constant flow rate, indicating excessive pressure being exerted at least at one location of the sinus membrane, then the shut-off procedure may be executed by the microprocessor. Flow rates for the saline solution from the sterile saline cartridge 16C using pressure sensing pump 16P may generally be controlled by a foot pedal 16F that may be coupled to controller circuitry within the pump. The more the surgeon depresses the pedal, the greater the flow rate of saline solution, which may be limited at a peak flow rate dictated by a governor, and which may be interrupted as discussed above during an overpressure situation.

Figure 8A:
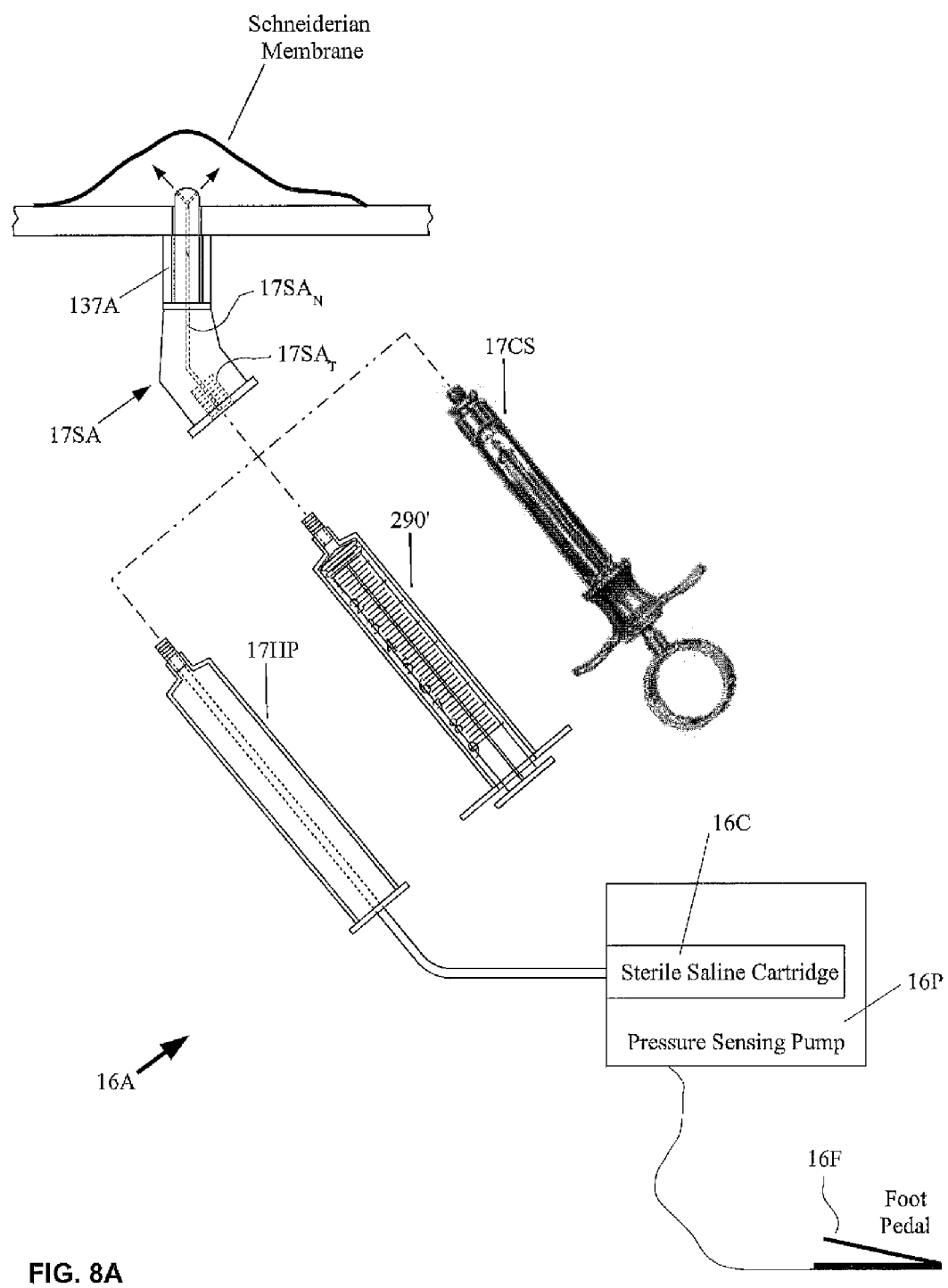
FIG. 8A is an alternative embodiment of the apparatus of FIG. 8, in which a tip that is fitted with a syringe adapter may alternatively receive a cartridge syringe for delivery of an anesthetic, or a plunger syringe for delivery of saline solution for lifting of the membrane, or may receive a hand piece that is coupled to the pressure regulated pump and sterile saline cartridge of FIG. 8 to accomplish lifting.

An alternative arrangement 17 is shown in FIG. 8A, which may also be utilized to introduce a measured amount of saline solution to cause lifting of the sinus membrane, but also offers other options. A tip may be received in the implant socket with the depth of its penetration being limited by a reduction cylinder 137A (described in Applicant's above mentioned co-pending application), and with the tip receiving in a conduit therein, the needle from a syringe adapter 17SA. The syringe adapter 17SA may be constructed generally in accordance with U.S. Pat. No. 5,514,113 to Anderson for "Angled Syringe Needle and Adapter therefore," the disclosures of which are incorporated herein by reference. However, rather than having the needle protrude past the end of the unit, as with the Anderson syringe adapter, the needle $17SA_N$ may terminate at the opening into which the internal threads $17SA_T$ are formed within syringe adapter 17SA. These internal threads $17SA_T$ may be used to receive one of several different delivery devices. A cartridge syringe 17Cs, which is known in the art and may receive anesthetic cartridges, may have an externally threaded end be received within the internal threading $17SA_T$ of syringe adapter 17SA. Alternatively, a syringe 290' may have a threaded outlet that may be threadably received within the internal threading $17SA_T$ of syringe adapter 17SA, with the plunger of the syringe being used for manual delivery of saline solution. As another alternative, a hand piece 17HP may have a threaded outlet that may be threadably received within the internal threading 17SA$_T$ of syringe adapter 17SA, with the hand piece having a tube being coupled to receive saline solution in a pressure-regulated and flow-rate-regulated manner from the saline cartridge 16C, using the pressure sensing pump 16P, as described hereinabove.

Figure 9A:
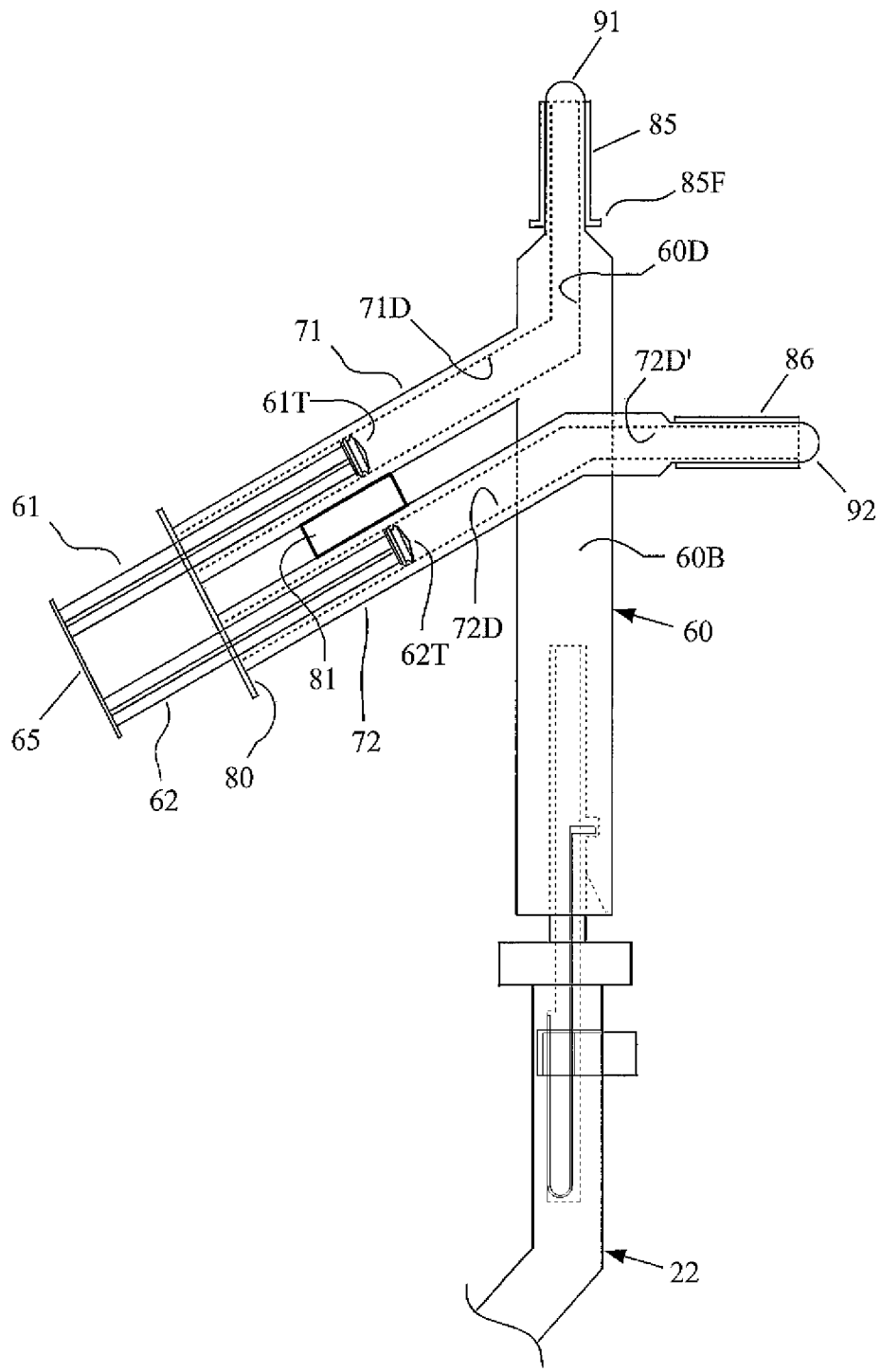
FIG. 9A is the support member of FIG. 1, with the redundant balloon tip of FIG. 5 being releasably received thereon, and with the synchronized plungers occupying in a first position, whereby the balloon are generally deflated.

FIG. 9A illustrates the tip 60 being releasably received upon the support member 22 of the Osteotome of the present invention, to be used for atraumatically elevating the sinus membrane. Tip 60 has been conceived and adapted to specifically permit such lifting of the Schneiderian membrane to occur in a controlled manner that has not yet been available to the oral surgeon, through the use of a dual balloon system. It is known in the art to utilize a balloon to gently and uniformly lift the Schneiderian membrane, which may reduce the incidence of perforation (see e.g., Muronoi M, Xu H, Shimizu Y, and Ooya K., "Simplified procedure for augmentation of the sinus floor using a haemostatic nasal balloon," British Journal of Oral & Maxillofacial Surgery 41(2); 120-121, 2003; and U.S. Pat. No. 7,396,232 to Fromovich for "Periosteal Distraction"). However, a drawback to this approach is that the oral surgeon does not have any positive visual indication of the amount of lifting that is occurring or that has actually already occurred by expansion of the balloon above the sinus floor to cause lifting. An indirect indication may be available through, for example, introduction into the balloon of a specific quantity of a filling fluid/material, as disclosed herein; however, the tip 60 of the present invention provides a means for positive visual indication and/or quantification of the expansion of the balloon and the resultant amount of lifting of the sinus membrane.

Tip 60, in addition to being adapted to be releasably received upon the support member 22 of handle 21, as described hereinabove, may include a first plunger 61 and a second plunger 62 that are each slidably received within a first barrel portion 71 and second barrel portion 72, respectively. The first and second barrel portions 71/72 may be secured to, or be integrally formed with, the body 60B of tip 60. The body 60S may, but need not necessarily be formed into a cylindrical shape.

The first barrel 71, as illustrated in FIG. 9A, is shown as having been integrally formed with the body 60B, and as having an inner cylindrical diameter 71D that continues into the center of the body 60B, where it is in fluid communication with a vertical conduit 60D, that may be cylindrical. The second barrel 72 is shown as being formed independent from body 60B, but may be secured relative to the first barrel 71 through the use of a flange 80 that is integral to, or attached to, the end of each of the first and second barrel sections 71 and 72. Attaching of the flange 80 to the barrel sections 71 and 72 may occur through the use of any suitable manufacturing process, including, but not limited to, adhesives, mechanical fasteners, etc. The second barrel 72 may be secured to the body 60B in a similar manner. In addition, stiffening flange 81 may be secured to both barrel sections 71 and 72. The securing of the second barrel 72 to the body 60B and the use of stiffening flange 81 are not necessary for the full functioning of tip 60 (see the embodiment 600 in FIG. 11), but may serve, when used, to provide additional stability to the arrangement. The flange 80 may satisfy the need to inhibit relative motion between first and second barrels 71 and 72, to permit the plungers within tip 60 to function as described hereinafter.

The vertical conduit 60D may extend all the way to the end of the body 60B, which may have a first balloon 91 thereon. The balloon may be integrally formed with the conduit or may be secured thereon using, for example, adhesive. The balloon 91 may alternatively be fixedly secured to the body 60B, which may taper in thickness at that location, and may utilize a sleeve 85, which may be secured upon the body using a friction fit, adhesive, or any other suitable means of retention.

The first end of each plunger 61 and 62 may have a compressible elastomeric tip member 61T/62T thereon, with each tip having a peripheral annular wiper that may form a satisfactory seal that engages with the inner diameters 71D/72D of the barrels, while exerting low resistance therein to the axial movement of the plungers. The second end of each plunger, being disposed outside of the barrels 71/72, may be secured relative to each other through the use of flange 65 that may be integral to, or be secured to, each of the first and second plungers 71 and 72, the same as for flange 80.

The second end of the second barrel section 72, being distal from the flange 80, may have a balloon 92 thereon. Balloon 92 may also be integrally formed with the barrel 72, retained upon which may taper in thickness at that location, or may be fixedly secured thereon through the use of a sleeve 86, which may itself be secured upon the barrel using a friction fit, adhesive, or any other suitable means of retention. The barrel section 72 may be straight, as seen for the embodiment 600 in FIG. 11, or it may have a bend, with the inner diameter 72D of the barrel transitioning into a second inner diameter 72D', which may be in fluid communication with the balloon 92.

Figure 9B:
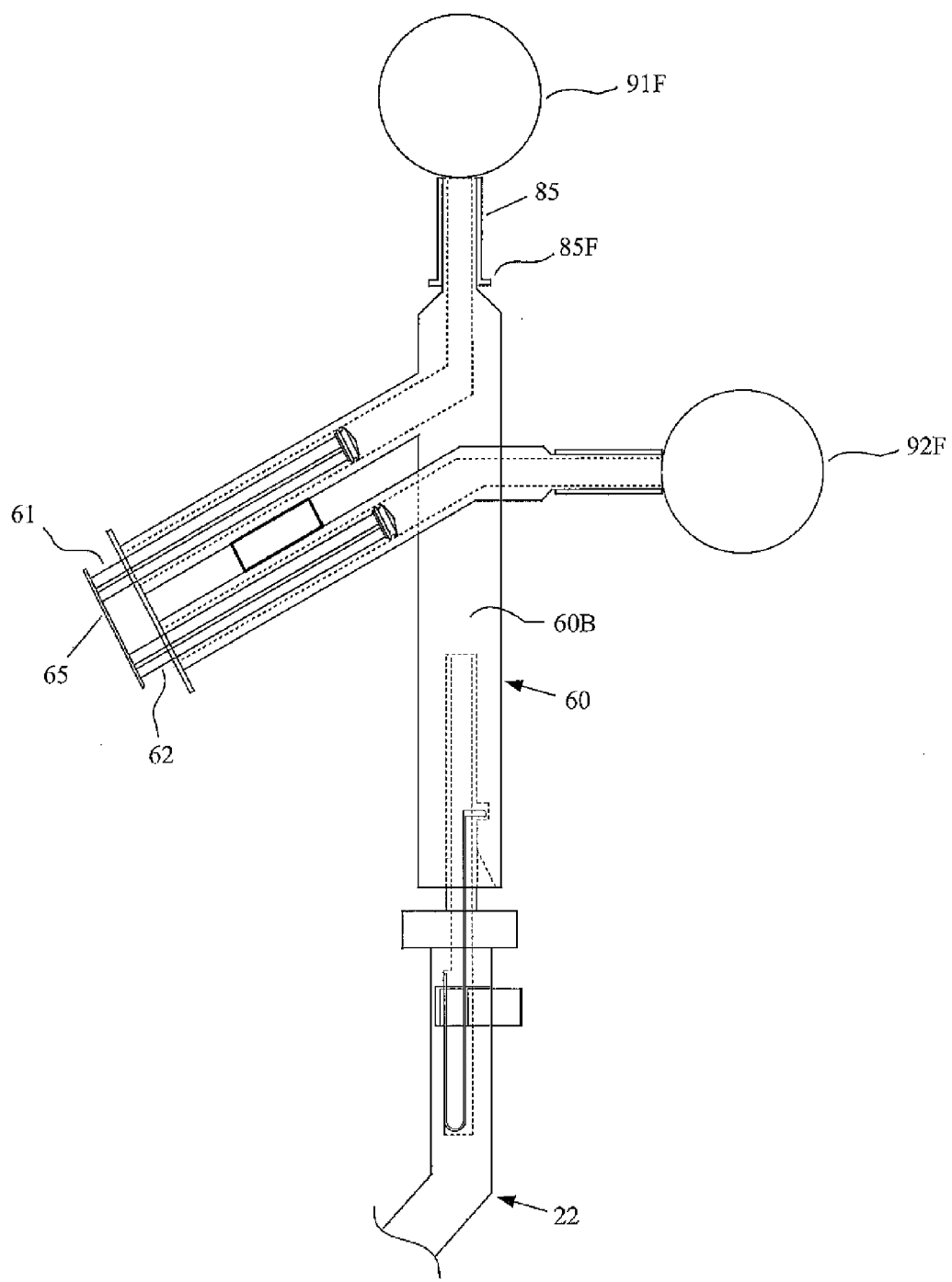
FIG. 9B is the support member and tip of FIG. 8A, but with the synchronized plungers in a second position, where the plungers a depressed part-way into the corresponding tubes, and the balloons are partially inflated.

With the tip 60 being so constructed, it may be seen by viewing both FIGS. 9A and 9B, that advancement of the plungers 71 and 72 may occur simultaneously through actuation of the flange 65 attached thereto, relative to the flange 80 that is attached to the barrel sections 71/72. This simultaneous actuation may cause both balloon 91 and balloon 92 to inflate at the same rate and to thus be virtually the same size, as seen for balloons 91F and 92F in FIG. 9B. Note that although the balloons 91 and 92 in FIG. 9A appear to be slightly inflated and protruding beyond the end of the sleeves 85/86, they were deliberately illustrated in that state in order to be instructive for the reader. Slight withdrawing of the flange 65 would cause complete deflation of the balloons in preparation for use of the tip 60.

Figure 9C:
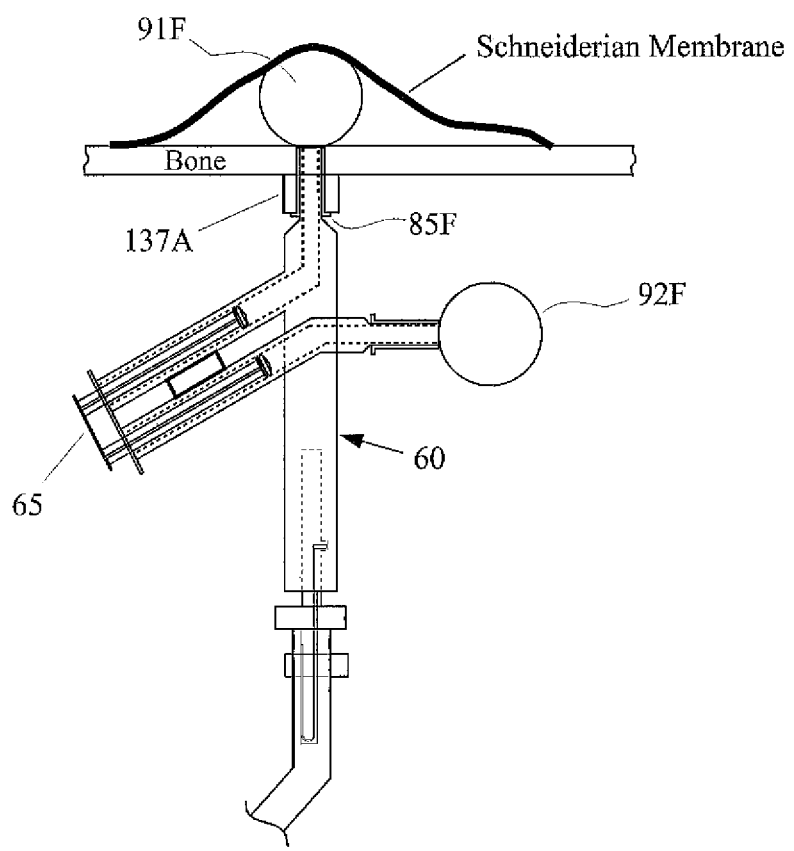
FIG. 9C illustrates the Osteotome with the redundant balloon tip, as seen in FIG. 8A, being used to atraumatically elevate the Schneiderian membrane.
Figure 9D:
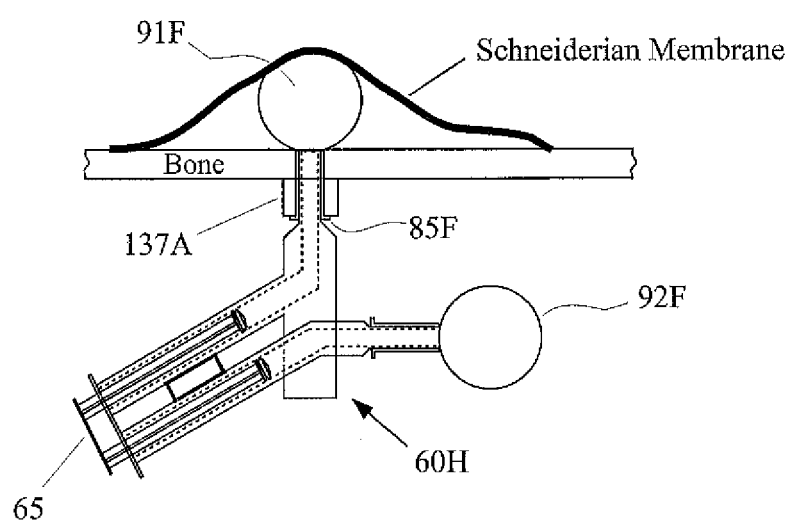
FIG. 9D illustrates use of the redundant balloon to both atraumatically elevate the Schneiderian membrane and to indirectly inform the surgeon as to the amount of lifting that has occurred, as seen in FIG. 8A, but where the dual balloon arrangement constitutes a separate member that is not utilized as a tip that is received upon a support member.

Use of the tip 60 for performing lifting of the sinus membrane is illustrated in FIG. 9C. A reduction cylinder 137A, as disclosed in Applicant's abovementioned co-pending application, may be positioned upon the balloon retention sleeve 85, to butt against the flange 85F, which may be an annular flange protruding outward from the cylindrical outer surface of the sleeve. Then, the sleeve 85 of tip 60 may be inserted into the implant socket, with the depth of insertion being limited by the length of the selected reduction cylinder 137A. As noted above, actuation of the flange 65 relative to the flange 80 may cause both balloon 91 and balloon 92 to inflate, with the inflation of balloon 91 causing lifting of the Schneiderian membrane, and with the duplicative inflation of balloon 92 providing the oral surgeon with positive visual indication of the amount of inflation that is occurring on the far side of the implant socket. Although some compression of the balloon 91 may be experienced when sandwiched between the membrane and the cortical floor, particularly if the balloon is inflated with air, which may tend to cause a size differential between the two balloons, the use of a fluid such as saline solution to cause inflation of both balloons would serve to diminish the size differential due to those compressive effects.

Figure 10:
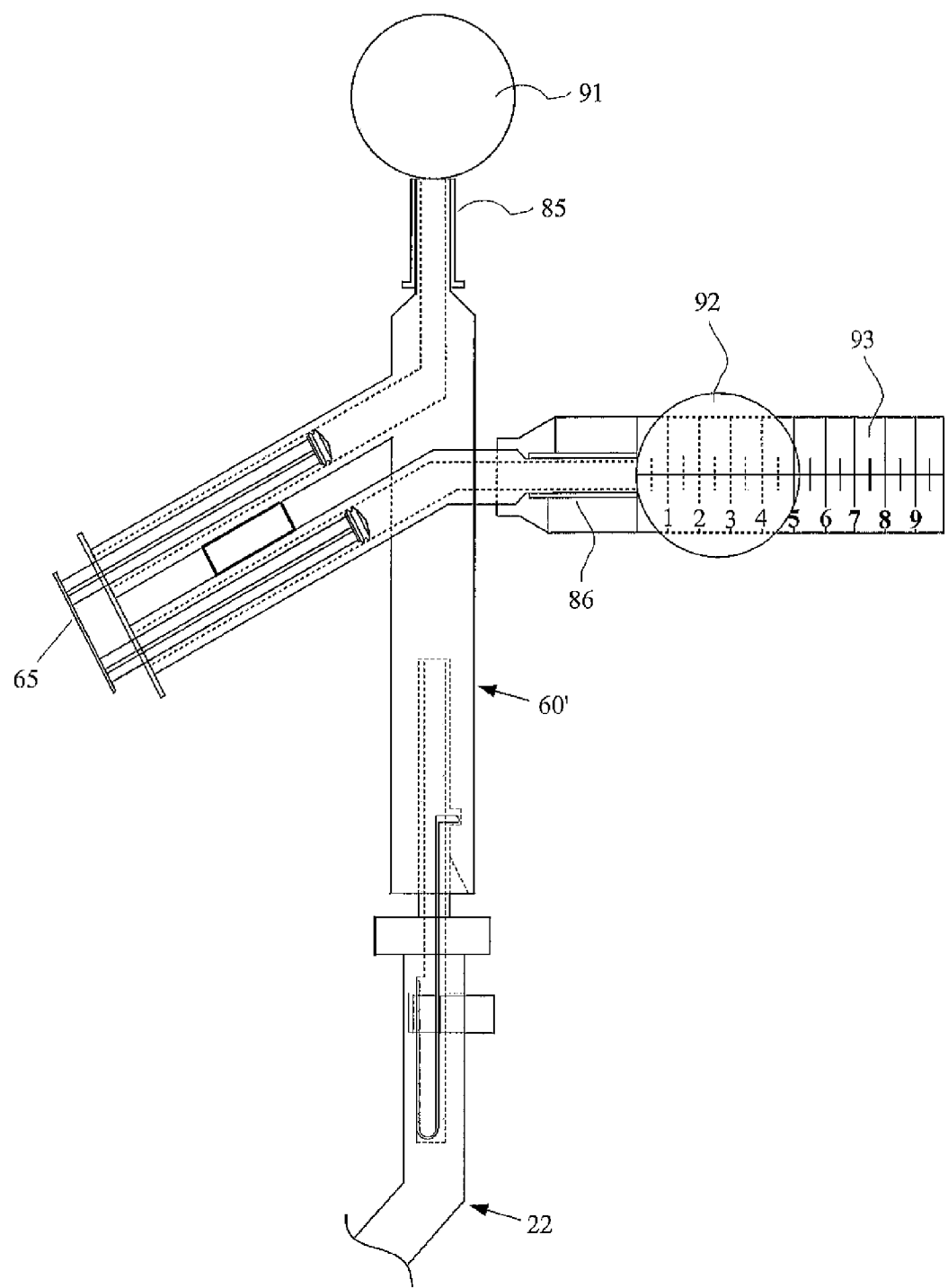
FIG. 10 is an alternate embodiment of the redundant balloon tip of FIG. 8A, which includes a scale having graduated markings thereon to provide a quantitative indication of balloon expansion and inflation.
Figure 10A:
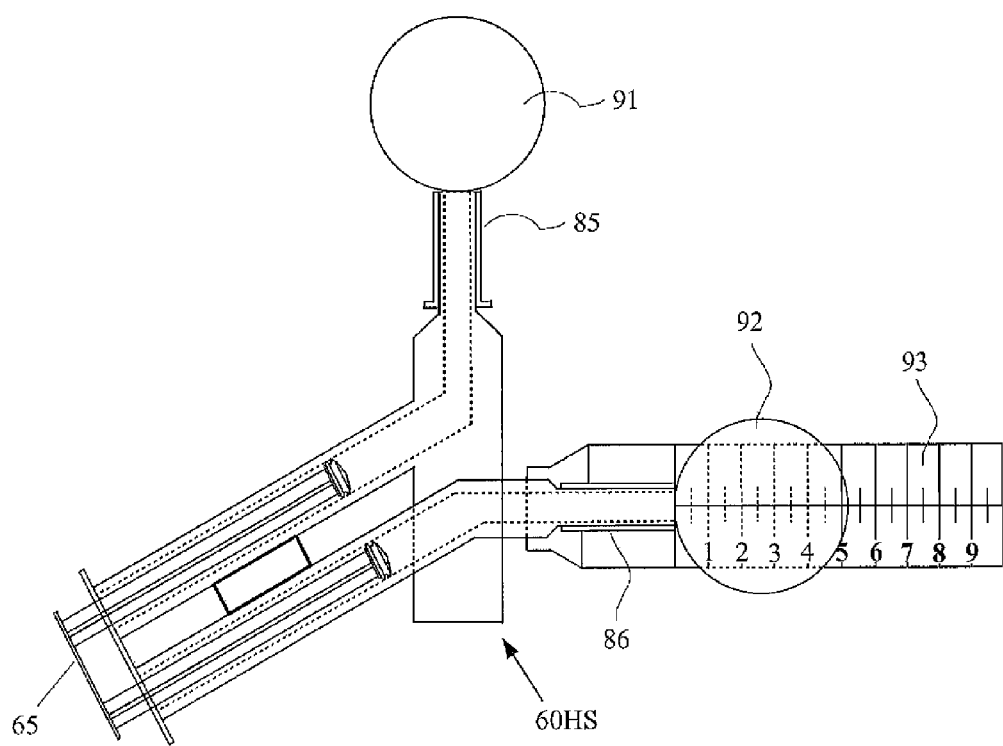
FIG. 10A is an alternate embodiment of the redundant balloon device of FIG. 10, but where the dual balloon arrangement constitutes a separate member that is not utilized as a tip that is received upon a support member.

In addition to utilizing the exposed second balloon 92 for providing a qualitative indication of the amount of expansion and lifting that is being provide by the first balloon 91 within the sinus cavity, a quantitative indication may also be provide to the oral surgeon. FIG. 10 shows an alternate embodiment of tip 60, being in the form of a tip 60', which may include a scale 93 having graduated markings thereon, with the markings of the scale beginning at the end of the sleeve 86, and progressing in the direction of the axis of the sleeve—in the direction that the balloon 92 would extend as it inflates. The markings may be in tenths and/or hundredths of an inch, or they may be in millimeters, or in such increments (whether English or Metric) that would be suitable to inform the oral surgeon as to the increasing diametrical size of the expanded balloon 92, and thus of the corresponding expanded balloon 91.

Figure 11:
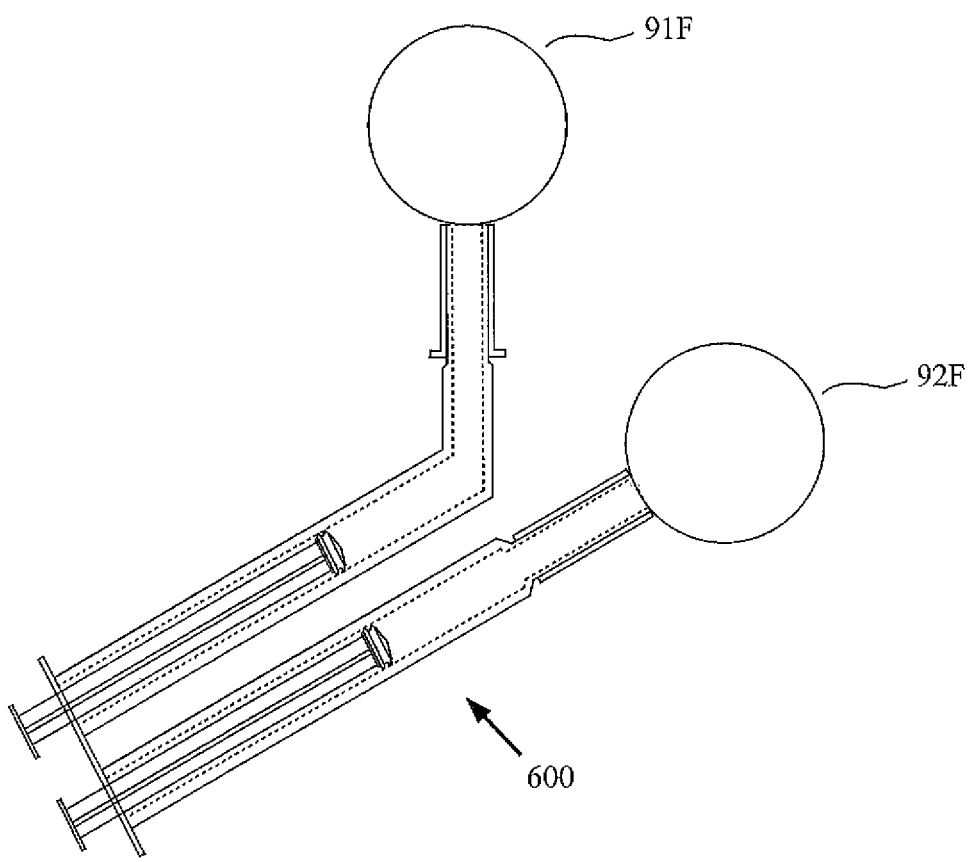
FIG. 11 is the dual balloon device of FIG. 8A, but adapted to be held directly by the oral surgeon, without use of the Osteotome handle and support member.

FIG. 11 illustrates a variation of the dual balloon device of FIG. 9A, which has been adapted into a device 600 that may be held directly by the oral surgeon, without use of the Osteotome handle and support member. It should be noted that the plungers, as shown therein, need not be fixedly secured to each other. However, this would necessitate that the oral surgeon exercise diligence to assure the manual advancement of the two plungers to occur as simultaneously as possible. This requirement may be relieved, by using graduated markings on the sides of the barrels, so that adjustments may be made to the amount of advancement made to the plunger inflating balloon 92F, so that it may precisely match the amount of advancement that was made to the other plunger.

Figure 12:
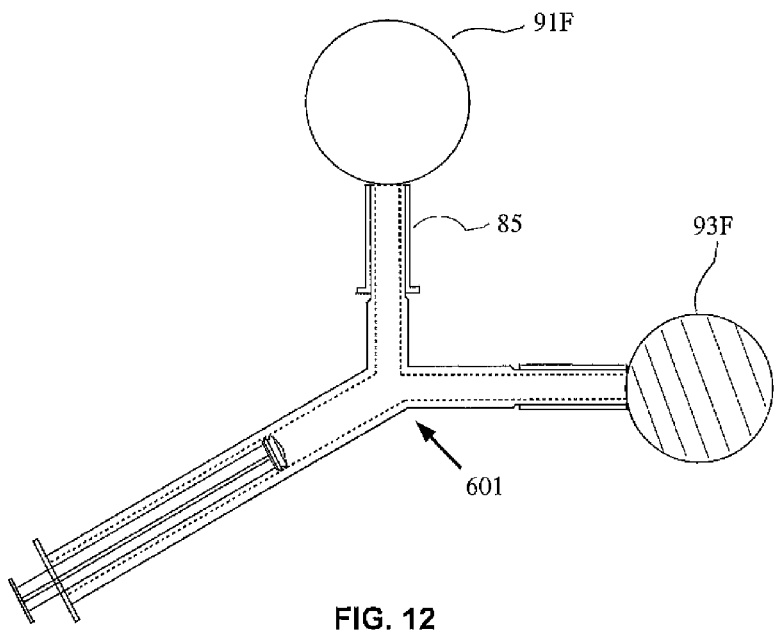
FIG. 12 is the dual balloon device of FIG. 10, but simplified to utilize only a single plunger for inflation of both balloons.

FIG. 12 is the dual balloon device of FIG. 11, but simplified into a device 601 that utilizes only a single plunger for inflation of both balloons, with the conduits leading into each of those two balloons being interconnected to the barrel that receives the plunger.

Figure 12A:
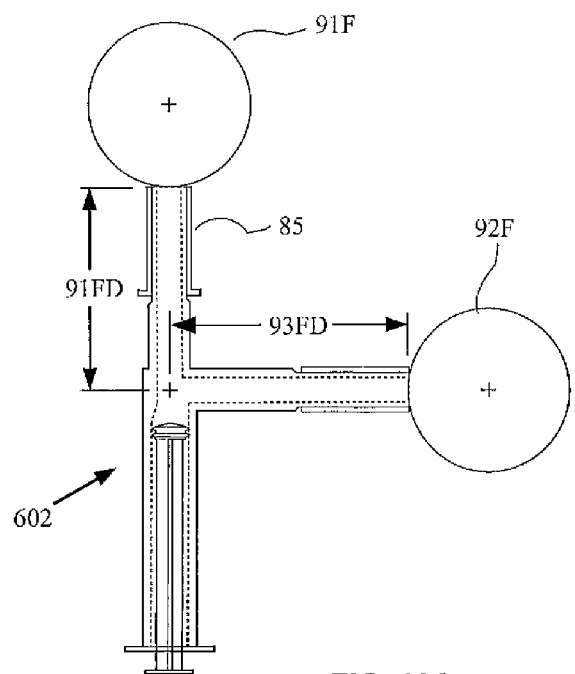
FIG. 12A is dual balloon device of FIG. 12, but where the first and second tubes in respective fluid communication with the first and second balloons are at a right angle, and are of equal lengths to better provide for equal inflation of the balloons, and more accurate indication by the second balloon of the lifting caused by the first balloon, and where the balloons are the same.

FIG. 12A is dual balloon device of FIG. 12, but where the first and second tubes in respective fluid communication with the first and second balloons are at a right angle. The conduits may also be constructed of equal lengths and inner diameters (where a cylindrical tube is used, although other conduit shapes may also be utilized), and the balloons may be constructed of the same materials and wall thicknesses, to better provide for more equal inflation of the balloons, and more accurate indication by the second balloon of the lifting caused by the first balloon.

With these arrangements, the pressure supplied to the balloon 91F by the sinus membrane may cause fluid in the barrel to be preferentially directed into the second balloon, particularly when lifting is first initiated, resulting in slightly dissimilar inflation rates. However, any small size differential in the inflated balloons due to this compressive effect may be effectively countered by using a second balloon 93F that is made of a different material having a different Young's Modulus or a balloon that is manufactured with a different wall thickness. The second balloon that does not experience any outside forces inhibiting its inflation and expansion may thus be empirically calibrated to have itself exert a greater resistance to inflation, to more closely match the actual conditions for inflation of the first balloon when inserted into the implant socket and acted upon by the membrane. Therefore, inflation of the balloons of the device 601 using the plunger, as seen in FIG. 12 (prior to having the sleeve 85 inserted into the implant socket), may result in greater diametrical inflation of balloon 91F than the diametrical inflation of balloon 93F.

Note other means of inflation for the first and second balloons may be used instead of the plunger/barrel combination, such as a foot pump, a squeezable hand pump, etc. A machine actuated pump may provide additional benefits in that it may be controlled by an electronic circuit and/or microprocessor to monitor pressure and flow of the fluid into the conduit(s) and the balloons, and may cause small incremental increases, which may be abruptly terminated in the event of a substantial pressure drop that may be indicative of a tear or perforation in the sinus membrane. A threaded plunger and barrel combination may also be used, whereby the fluid flow into the balloons may be induced by turning of the plunger within the barrel.

Figure 13:
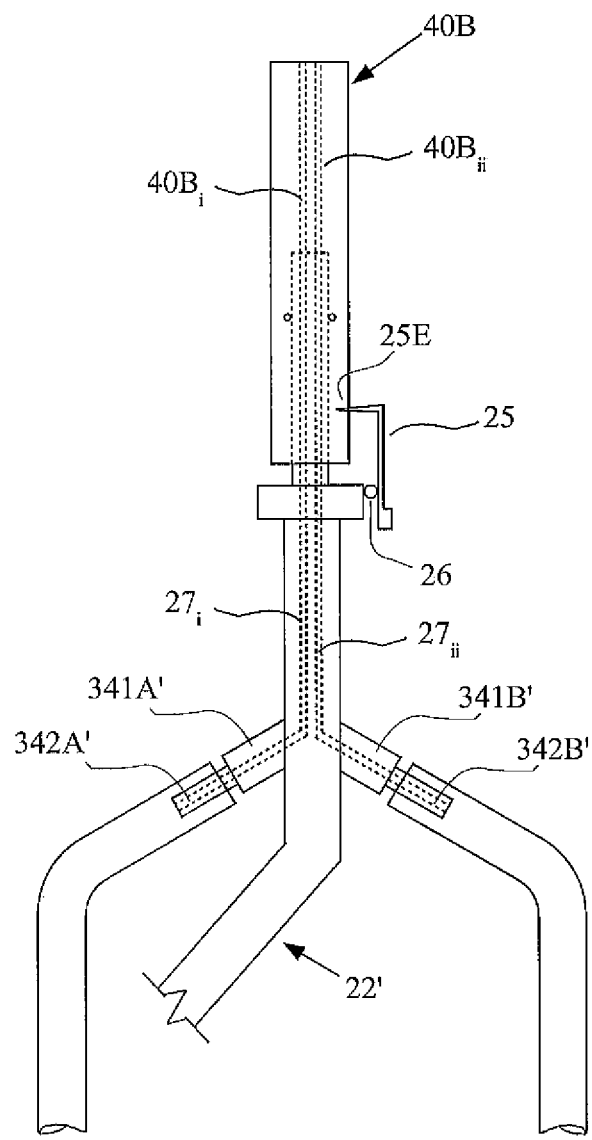
FIG. 13 illustrates an alternative embodiment for releasable attachment of a saline delivery tip of the present invention onto a support member, whereby the tips are adapted to be disposable.

FIG. 13 illustrates an alternative embodiment for releasable attachment of a saline solution delivery tip of the present invention onto a support member, whereby the tips are adapted to be disposable. The tip 40B may be received onto the cylindrical or keyed cross-sectional shaft of the support member 22', as described hereinabove, and may be retained thereon using a biased lever arm 25. The lever arm 25 may be pivotally attached to the support member 22' using a hinge 26 that may also support a torsion spring to cause biasing of the lever arm towards the shaft of the support member 22'. Instead of a torsion spring, a tension or compression spring may be used at the appropriate side of the lever arm to cause such biasing. An end 25E of the lever arm 25 may be received within a recess in the tip 40B to prevent inadvertent removal of the tip from the support member, and also prevent unwanted rotation of the tip 40B, when the cylindrical shaft is used. Tip 40B may be constructed to have dual conduits 40Bi and 40Bii therein, which is also seen within FIG. 3E. The dual conduits 40Bi and 40Bii may be in fluid communication with dual conduits 27i and 27ii in support member 22', which may permit separate inflow and outflow, using ports 341A' and 341B', respectively, of saline solution into and out from the area above the sinus floor of a patient, as discussed in other embodiments of the present invention.

Figure 14:
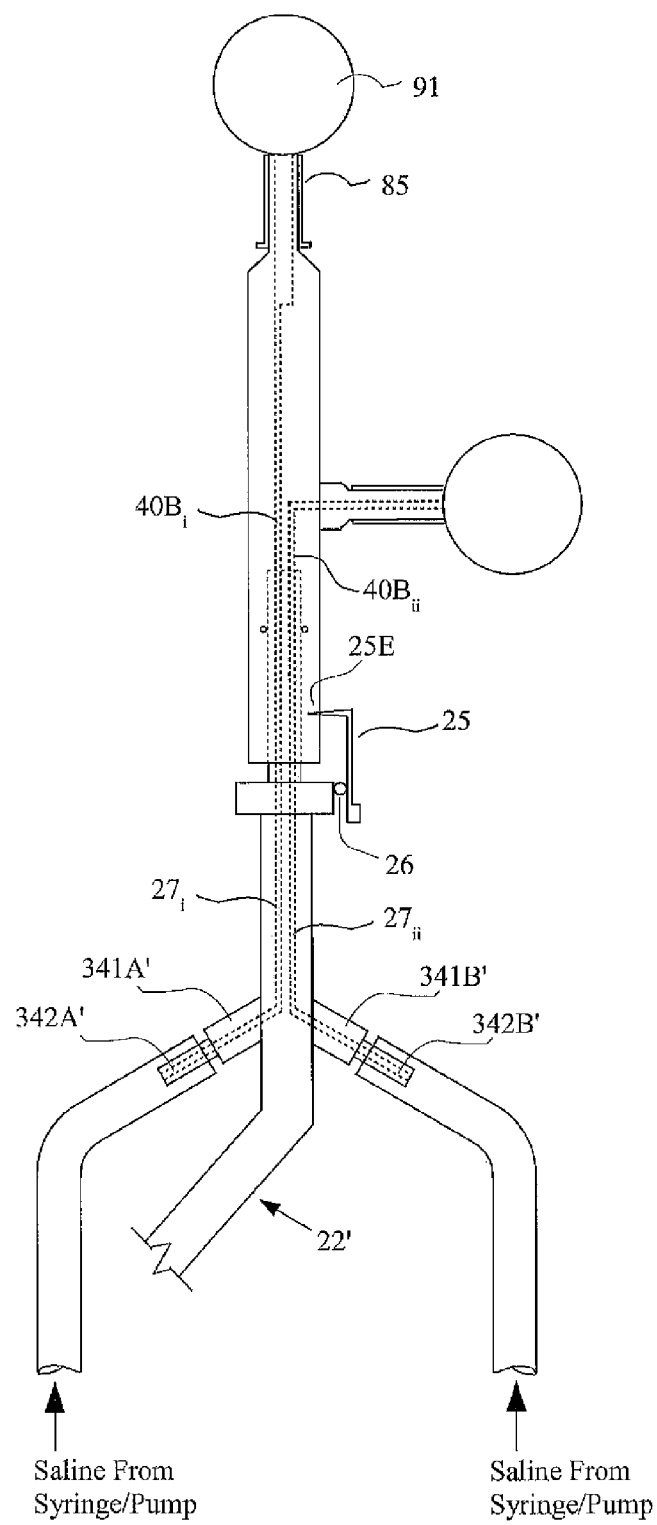
FIG. 14 illustrates the releasable attachment embodiment of FIG. 12, but with a disposable dual-balloon tip of the present invention being releasably received upon the support member.

FIG. 14 illustrates an alternate embodiment of the dual balloon tip of the present invention that may be mounted using the support member 22' and lever arm 25 of FIG. 13, and may receive saline solution therein for causing its inflation, using the dual conduits therein.

Figure 15:
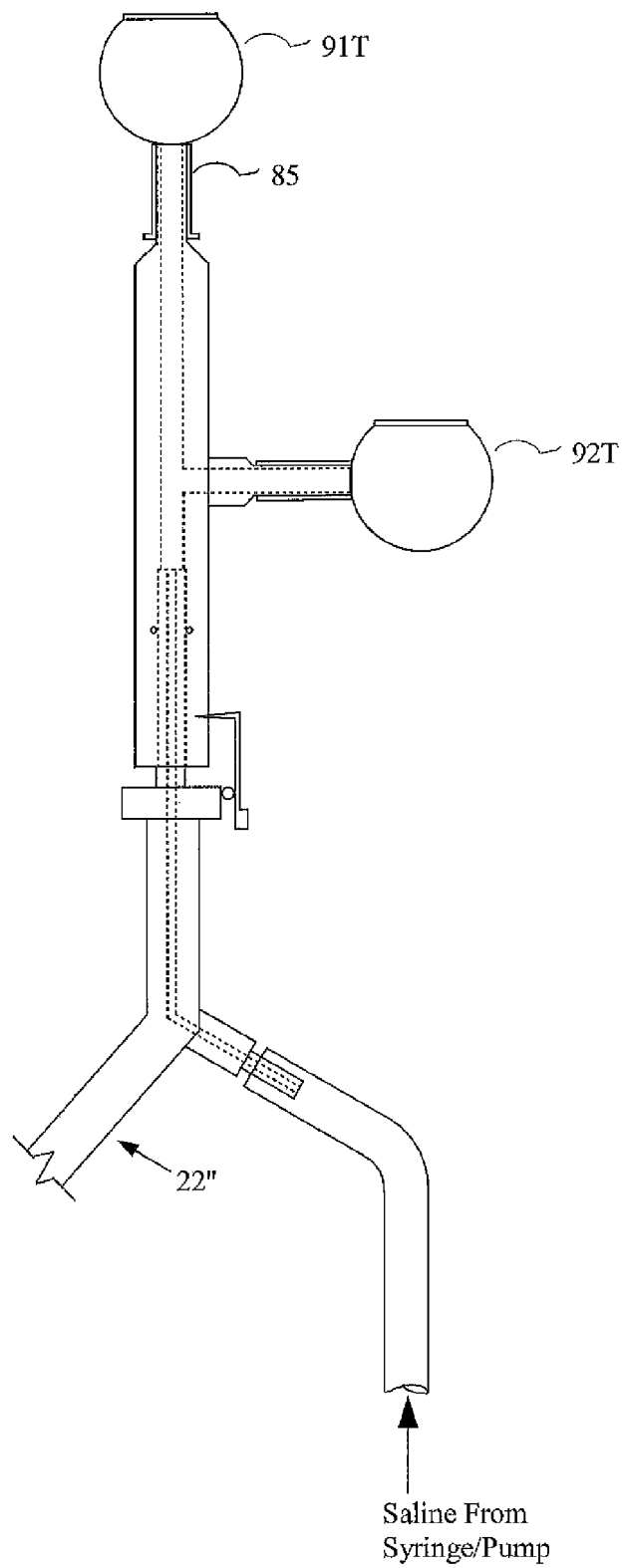
FIG. 15 illustrates the releasable attachment embodiment of FIG. 12, but with a disposable flat-topped dual-balloon tip of the present invention being releasably received upon the support member.

FIG. 15 illustrates an alternate embodiment of a dual balloon tip of the present invention, which may be mounted using a support member 22" and lever arm 25 that is similar to that of FIG. 13, but only utilizes one port for supplying of saline solution to the two balloons. The balloons 91T and 92T used therein may also be configured to have a generally flat top.

Figure 16:
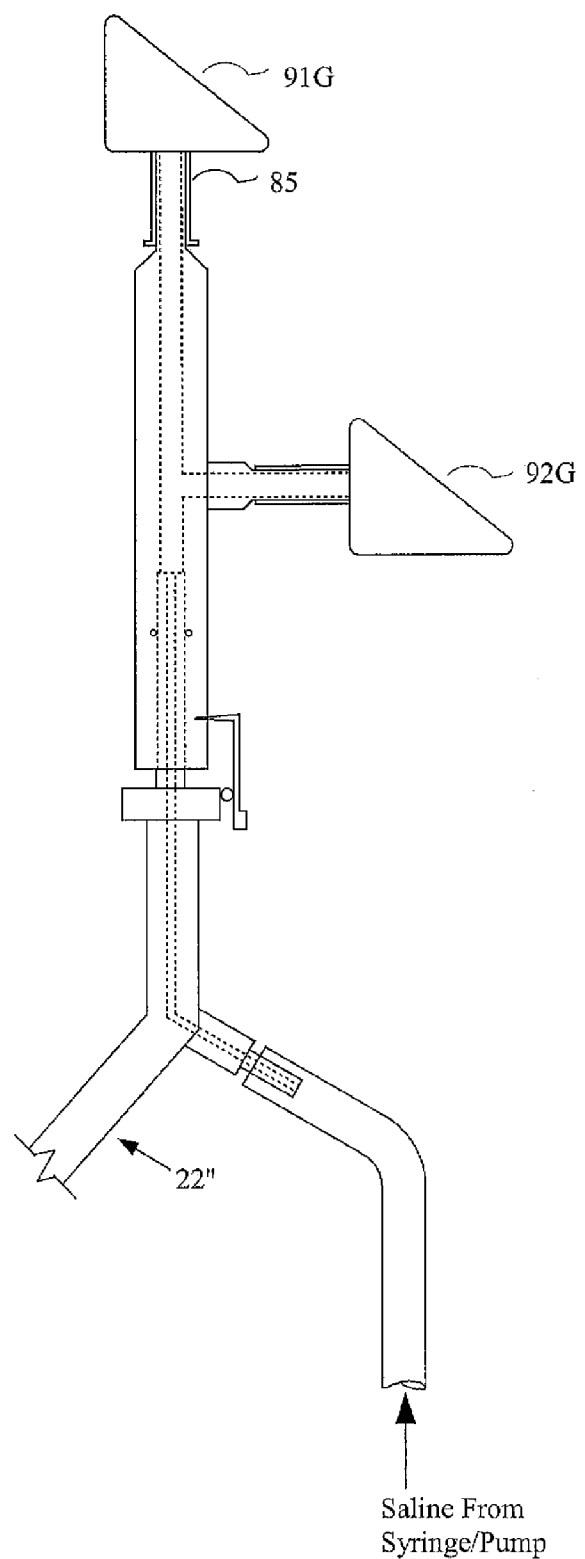
FIG. 16 illustrates the releasable attachment embodiment of FIG. 12, but with a disposable triangular-shaped dual-balloon tip of the present invention being releasably received upon the support member.

FIG. 16 illustrates an alternate embodiment of the dual balloon tip of FIG. 15, but where the two balloons may each be configured to have a generally triangular shape once they are inflated.

Figure 17:
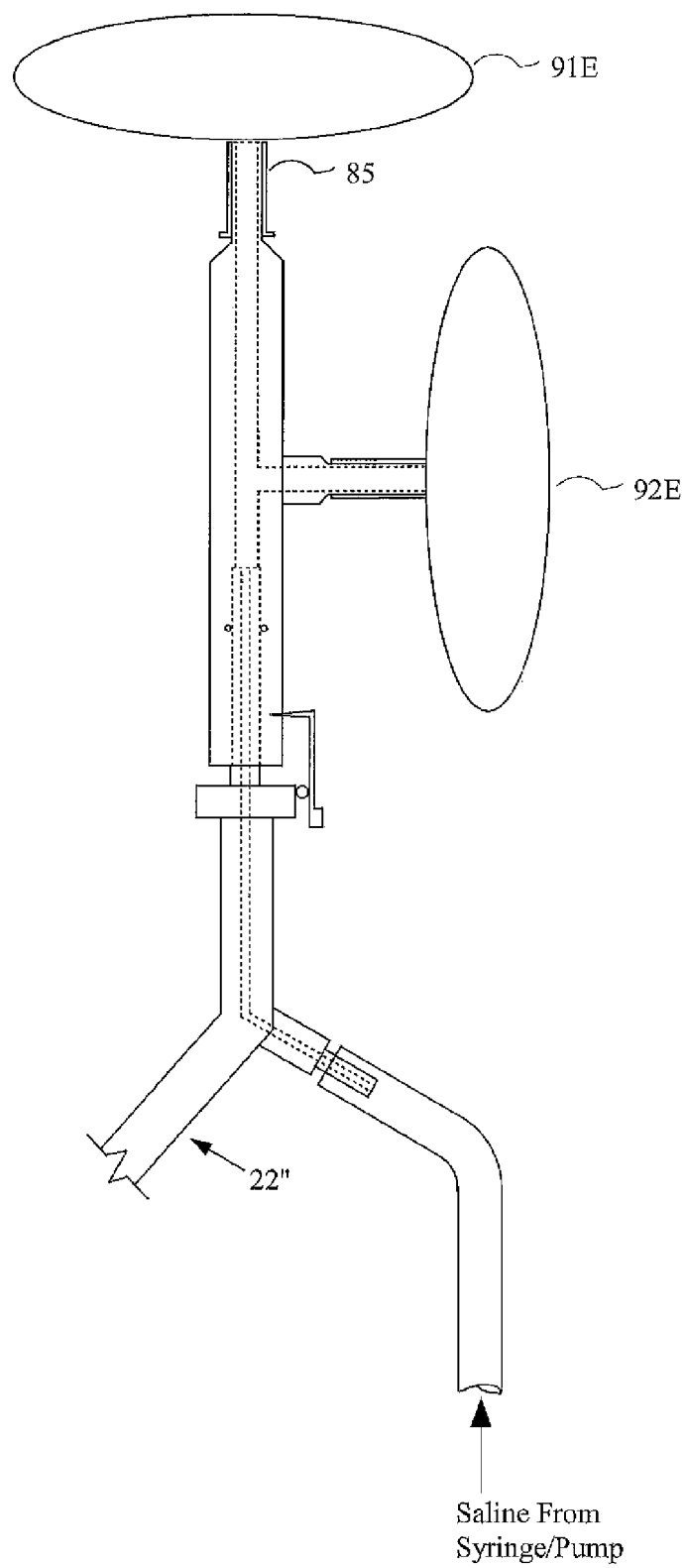
FIG. 17 illustrates the releasable attachment embodiment of FIG. 12, but with a disposable oval-shaped dual-balloon tip of the present invention being releasably received upon the support member.

FIG. 17 illustrates an alternate embodiment of the dual balloon tip of FIG. 15, but where the two balloons may be configured to have a generally oval or elliptical shape once they are inflated.

FIG. 18 illustrates an Osteotome arrangement 18 that may include the handle 11 discussed hereinabove, which may releasably receive a support member 122. Support member 122 may include a barrel portion 123 that may have an upper end 123U and a lower end 123L. The barrel 123 in proximity to the upper end 123U may be cylindrical, or it may have a slight conical shape, increasing in diameter with increasing distance from upper end 123U, but is represented throughout the following figures as being cylindrical. The cylindrical barrel portion 123 may have external threading thereon to provide adjustability to an internally threaded stop member 135 that may be used to limit the depth that the barrel may penetrate into the implant socket of a patient, as discussed hereinafter. The threaded stop member 135 may also be secured upon the barrel portion using a friction fit. The barrel portion 123 may have a conduit 124 therein that may run from the upper end 123U to the lower end 123L. A portion of the conduit 124 may comprise internal threading 123T$_I$ to enable the tips to be threadably received therein. To be representative, FIG. 18A and the subsequent figures are illustrated with internal threading 123T$_I$ shown within conduit 124 in proximity to the lower end 123L of the barrel portion 123.

Figure 18B:
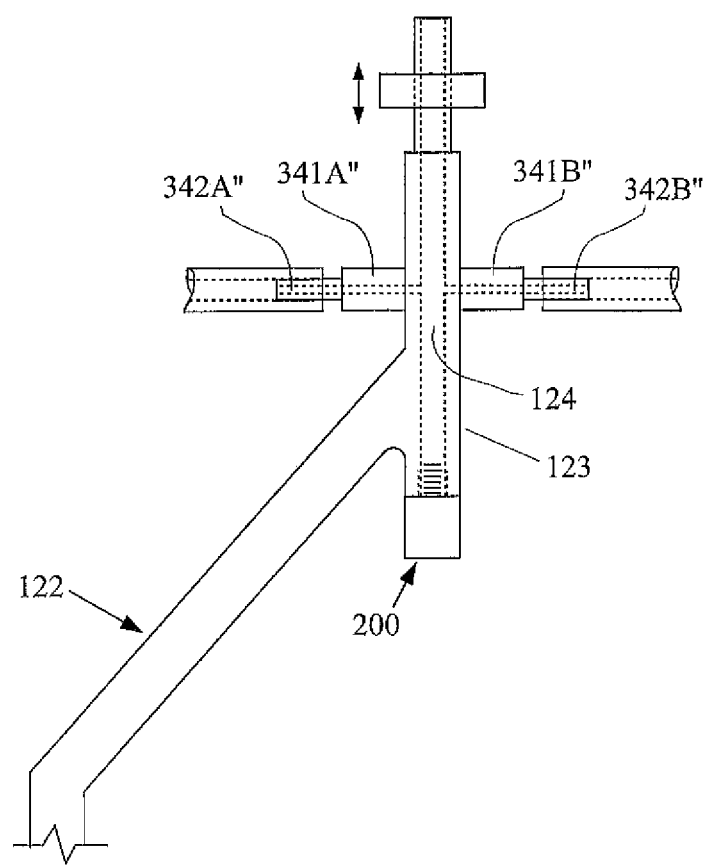
FIG. 18B illustrates the Osteotome arrangement of FIG. 18, but with a first and second tube being connected to its first and second ports, and with the conduit of the barrel section being sealed by a plug.

Protruding from opposite sides of the barrel portion may be a first port 341A" of first connector 342A", and a second port 341B" of second connector 342B", each of which may be adapted to receive a tube, as discussed hereinabove, or to be capped using a threaded cap member 380C. The connectors 342A" and 342B" may each be in fluid communication with the conduit 124. Where either or both of the connectors 342A" and 342B" are to be used according to the previously discussed processes, the bottom of the conduit 123 may be sealed using plug 200 (FIG. 18B). Plug 200 may include an externally threaded shaft 200T that may be threadably received within the internal threading 123T within conduit 124 of the barrel portion 123.

Osteotome arrangement 18 is also particularly adapted for assisting an oral surgeon in performing many different steps of the sinus lift procedure, through the use of tips 201, 202, 203, 204, 205, and 206, which are shown collectively in FIG. 18A. Insertion of the tip 201 into the barrel portion 123 is illustrated in FIG. 19A, with its use during the sinus augmentation procedure shown within FIG. 19. As seen in FIG. 19, with the upper end 123U of the barrel portion having been secured within the implant socket of a patient's alveolar ridge, the tip 201 may be rotated. The threaded engagement between the external threads 201T$_E$ on the shaft 201S of tip 201 and the internal threads 123T$_I$ of the barrel portion 123 may thereby cause the convex end 201V of the tip 201 to impinge upon the cortical layer to cause up-fracturing of the remaining 1-2 millimeters of remaining bone thickness thereat. The bottom end 201B of the tip 201 may simply be the flat end of a cylinder, the same as end 200B for plug 200 (FIG. 18A), or it may transition into a flange 201F extending therefrom to provide a graspable handle portion for the oral surgeon to better grasp the end of the tip 201, to more easily cause its rotation during up-fracture of the cortical layer. The length of the shaft 201S of the tip 201 may be coordinated with the length of the barrel section 123 between upper end 123U and lower end 123L, as seen in FIG. 19, such that when the tip 201 is fully engaged with the barrel section, the convex end 201V of the tip 201 may only protrude a small distance from the upper end 123U of the barrel section 123. The distance that it protrudes may be only slightly longer than is necessary to cause up-fracturing of the cortical layer.

Figure 20A:
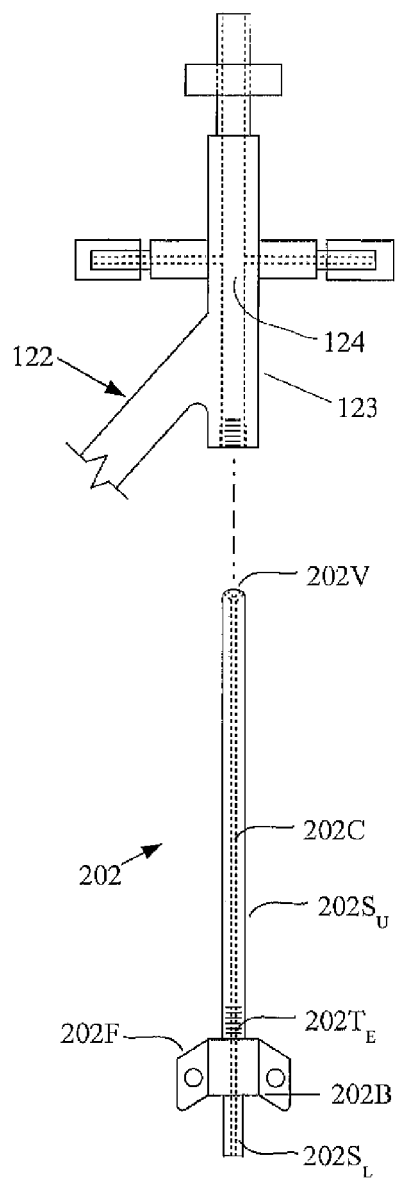
FIG. 20A is an exploded view of the barrel portion of the Osteotome of FIG. 20 and of the tip shown in FIG. 20.

Tip 201 may be removed from the Osteotome, and tip 202 may next be inserted within the conduit 124, as seen in FIG. 20A. Tip 202 may have a convex end 202V on the end of a shaft 202S$_U$, with external threading 202T$_E$ on a lower portion of the shaft, similar to tip 201. Tip 202 may have a shaft portion that may extend beyond the bottom 202B of a cylindrical base portion to form a lower shaft portion 202S$_L$. In addition, tip 202 may also have a conduit 202C that may run the entire length of the tip, from the convex upper end 202V of the upper shaft 202S$_U$ to the lowermost portion of lower shaft 202S$_L$. At the convex upper end 202V, the conduit 202C may, rather than terminating in a single opening, split to form a dual opening, or split a quad opening, or even five openings (see e.g., FIGS. 6A and 6B).

Figure 20:
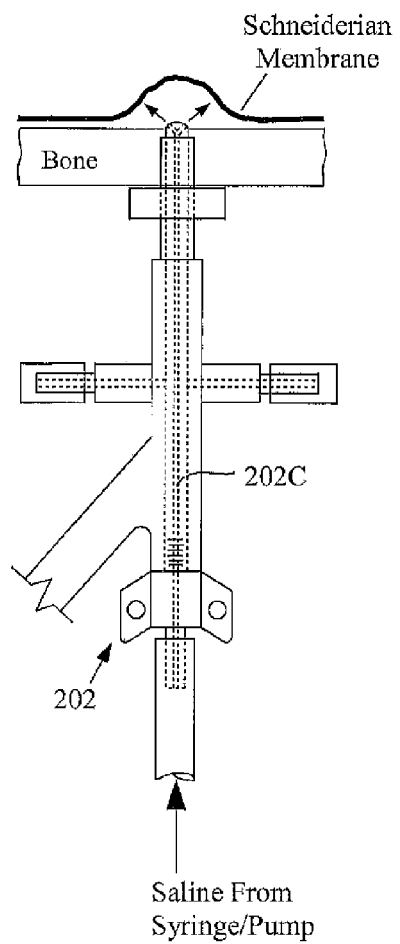
FIG. 20 illustrates the Osteotome of FIG. 18 being received within the bone of the alveolar ridge, and with a third tip of the series of tips being received within the barrel portion to be used to deliver saline solution to cause lifting of the sinus membrane.

With the upper end 123U of the barrel portion of the Osteotome having been secured within the implant socket of a patient's alveolar ridge, and with the tip 202 being threadably engaged within the barrel section 123, as seen in FIG. 20, a tube may be connected to the lower shaft 202S$_L$, and may thereby supply saline solution through the conduit 202C, which may exit through the openings to cause lifting of the sinus membrane. Multiple openings in the end of the convex end 202V of the tip 202 may be preferable, so as to distribute the lifting force provided by the stream of saline across a greater surface area of the sinus membrane, to thereby have less of a tendency towards causing a perforation. As an alternative to the utilization of tip 202 for lifting of the membrane by saline solution carried therein, tip 206 may instead be inserted within the conduit 124, and expansion of its foam sponge 206S beyond the end of the conduit may serve to elevate the membrane. The threading 207R of tip 207 may have graduated markings thereon to identify the depth that the foam has been inserted to cause lifting. Tip 207, which may have a micro camera 207C secured within its end, may be inserted into the conduit 124 and may be used therein to visually observe the integrity of the membrane and assure that no tears or perforations have occurred. Suitable micro camera technology has been developed by, and may be available from the partnership of Awaiba GmbH and the Fraunhofer Institute, or alternatively, fiber optic imaging may be used. In addition, a radio opaque fluid material may also be similarly introduced beneath the elevated membrane, and digital radiography may be used to determine the topographic elevated heights of the membrane in three-dimensions using CT imaging.

Tip 202 may be removed from the barrel section 123 of the Osteotome, and tip 203 may next be inserted within the conduit 124, as seen in FIG. 21A. Tip 203 may be constructed similar to tip 202, having a shaft 203S terminating at a convex end 203V, and which extends upward from a cylindrical base, and also having a conduit 203C therein. However, the bottom 203B of the cylindrical base may have a threaded opening 203T$_{SA}$ therein to serve as a syringe adapter, and permit coupling of a syringe 490 thereto. The threaded opening 203T$_{SA}$ may be in fluid communication with the conduit 203C. With the upper end 123U of the barrel portion 123 of the Osteotome having been secured within the implant socket of a patient's alveolar ridge, and with the tip 203 being threadably engaged within the barrel section 123, and with the syringe 490 received within the syringe adapter, as seen in FIG. 21, the syringe may be used to deliver bone particles into the region above the sinus floor.

Figures 22, 22A, 22B:
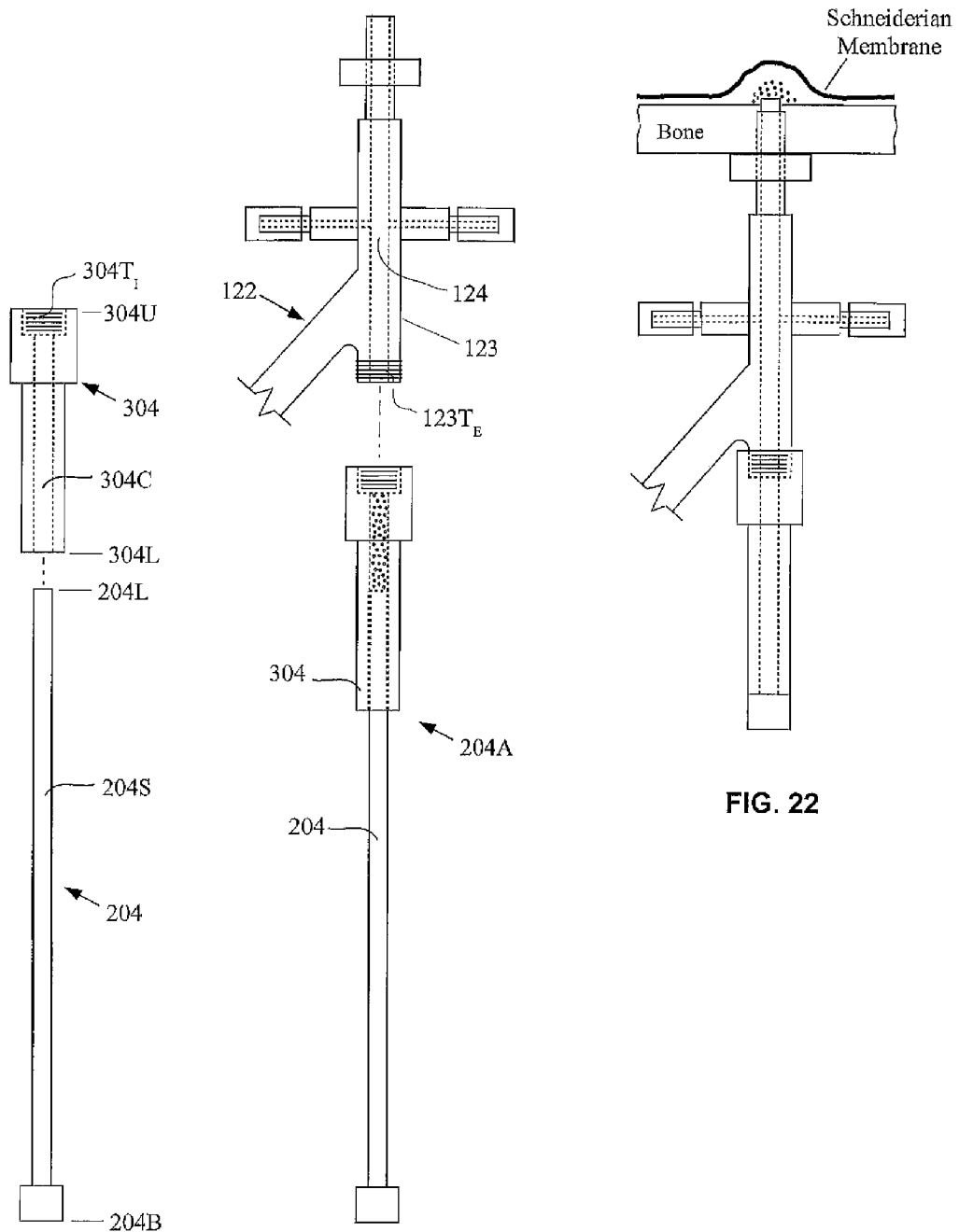
FIG. 22 illustrates the Osteotome of FIG. 18 being received within the bone of the alveolar ridge, and with a fifth tip—a bone carrier assembly tip—being received within the barrel portion to be used to deliver bone fragments using a sleeve and a plunger.
FIG. 22A is an exploded view of the barrel portion of the Osteotome of FIG. 18 and of the bone carrier assembly tip shown in FIG. 22.
FIG. 22B is an exploded view of the parts comprising the bone carrier assembly tip of FIG. 22A.

The bone delivery assembly 204A of FIG. 22A may include a tip 204 and a bone carrier 304 (FIG. 22B). Tip 204 may be constructed generally the same as tip 201 (with or without the graspable flange), and may thus include a shaft 204S extending from a cylindrical base, but terminating at an end that may be a general flat end 204L. The bone carrier 304 may be a sleeve having a conduit 304C therein that may extend from the lower end 304L of the carrier and up through the upper end 304U, and which may be sized to slidably receive the shaft 204S of tip 204 therein. The conduit at upper end 340U of the bone carrier may be subsumed by an opening therein that may be larger than the conduit 304C, and which may have internal threading 304T$_I$. The bone carrier assembly 204A may have the tip 204 positioned relative to the bone carrier 304, as seen in FIG. 22A, such that an application of bone particles may be retained within the conduit 304C of the carrier. The bone carrier assembly 204A may be so arranged, including the addition of the bone particles therein, by the practitioner in the office prior to performing the implant procedure, or it may be so arranged and provide to the practitioner by a commercial supplier.

With the upper end 123U of the barrel portion of the Osteotome having been secured within the implant socket of a patient's alveolar ridge, the bone carrier assembly 204A may be threadably connected to the barrel section 123, by threadably engaging the internal threading 304$T_I$ of the carrier 304 with the external threading 123$T_E$ in proximity to the lower end 123L of the barrel portion. By inserting the tip 204 all the way into the conduit of carrier 304, the bone particles that had been contained within the carrier may be delivered into the region above the sinus floor, as seen in FIG. 22.

Figure 23A:
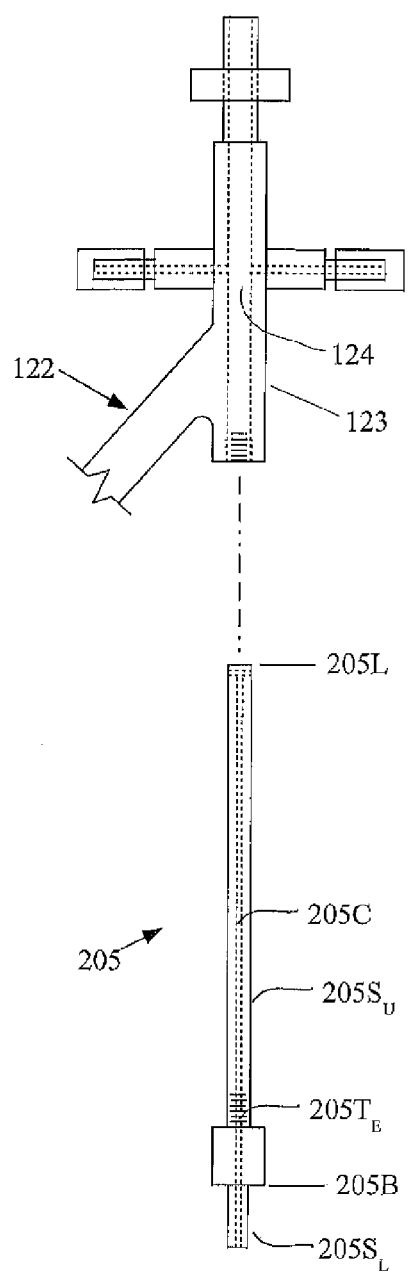
FIG. 23A is an exploded view of the barrel portion of the Osteotome of FIG. 23 and of the tip shown in FIG. 23.

Bone carrier assembly 204A may then be removed from the barrel section 123 of the Osteotome by threadably disengaging the carrier 304 therefrom, and tip 205 may next be inserted within the conduit 124, as seen generally in FIG. 23A. Tip 205 may be constructed similar to tip 202, but instead of having upwardly directed openings at the end 202V, it may have laterally directed openings.

Figure 23:
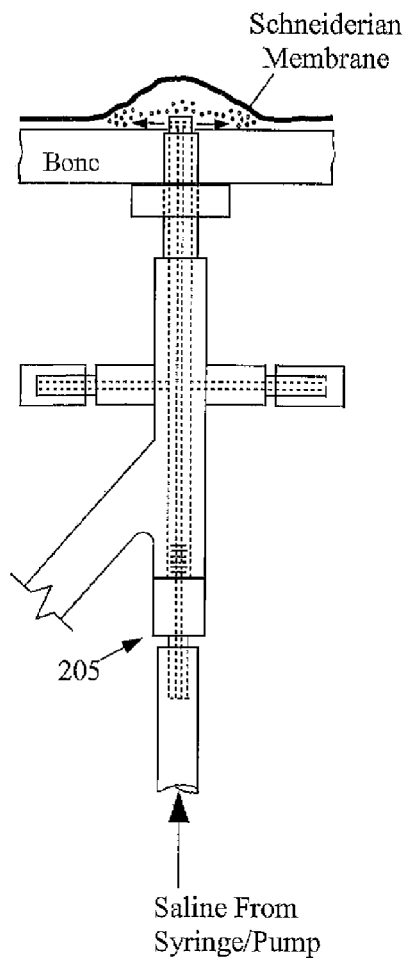
FIG. 23 illustrates the Osteotome of FIG. 18 being received within the bone of the alveolar ridge, and with a sixth tip of the series of tips being received within the barrel portion to be used to deliver saline solution to laterally spread the bone fragments and/or to cause further separation of the sinus membrane from the cortical floor.

With the upper end 123U of the barrel portion of the Osteotome having been secured within the implant socket of a patient's alveolar ridge, and with the tip 205 being threadably engaged within the barrel section 123, as seen in FIG. 23, a tube may be connected to the lower shaft 205$S_L$, and may thereby supply saline solution through the conduit 202C, which may exit laterally through the openings to cause spreading of the bone particles and/or cause further separation of sinus membrane in the lateral direction. Multiple openings near the conduit at the end of the flat end 205L of the tip 205 may be preferable, so as to generally distribute the saline radially about the sinus floor.

FIG. 19C illustrates a tip that may resemble the bone carrier assembly externally, but tip 211 may in fact be a piezotome that may be constructed to permit its threaded engagement with the Osteotome of FIG. 18 to be used in ultrasonic cutting through the remaining 1-2 mm of the cortical bone layer to carefully reach the sinus membrane. With the upper end 123U of the barrel portion of the Osteotome having been secured within the implant socket of a patient's alveolar ridge, and with the tip 211 having some initial threaded engagement within the barrel section 123, as seen in FIG. 19B, activation of the piezotome by supplying power to its power cord 211P and continued rotation of the tip 211, may cause cutting through the bone and advancement of the end 211U. The advancement may continue until the cortical layer is penetrated. Graduated markings 211M may be used on the outside of the barrel portion 123 to inform the oral surgeon as to the amount of advancement that has occurred, to prevent perforation of the sinus membrane.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

I claim:

1. An osteotome comprising:
a replaceable tip member, said tip member having a first end and a second end, said tip member comprising:
an orifice configured to begin at said second end of said tip member and to extend in an axial direction of said tip member to end a portion of the way to said first end;
a first conduit beginning proximate to said first end of said tip member and configured to extend in the axial direction of said tip member, and to terminate between said first end of said tip member and said end of said orifice;
a first hydration port, said first hydration port comprising a second conduit configured to be in fluid communication with said first conduit, and said first hydration port comprising coupling means for releasably receiving a hose thereon to be in fluid communication with said second conduit;
a second hydration port, said second hydration port comprising a third conduit configured to be in selective fluid communication with said first conduit, and said second hydration port comprising coupling means for releasably receiving a hose thereon, to be in fluid communication with said third conduit,
a first hose, a first end of said first hose coupled to said means for releasably coupling of said first hydration port;
a second hose, a first end of said second hose coupled to said means for releasably coupling of said second hydration port;
means for selectively receiving and measuring an amount of fluid, being coupled to said second end of said second hose, and configured for alternately blocking the fluid flow from said first conduit into said third conduit, and permitting and measuring the fluid flow therebetween; and
means for infusing a measured amount of fluid, being coupled to said second end of said first hose, for infusing the measured amount of fluid through said second conduit and said first conduit, and out said opening at said first end of said tip member above a sinus floor cortical bone to elevate the sinus membrane;
and
a body, said body comprising:
a support portion, said support portion comprising:
a protrusion, said orifice of said tip member configured to releasably receive said protrusion of said support portion of said body therein, to releasably mount said tip member to said body;
means for releasably securing said tip member to said support portion; and a graspable handle portion.

2. The osteotome according to claim 1, wherein said replaceable tip member comprises:
a cylindrical outer surface; and
a plurality of sharp prongs configured to protrude from said first end of said tip, and said plurality of prongs disposed on said first end to be equally spaced about a circumference of said cylindrical outer surface; said plurality of sharp prongs configured to be rotated by said body being rotated, to score the cortical layer in preparation for up-fracture of the remaining cortical layer.

3. The osteotome according to claim 2, wherein each of said plurality of sharp prongs comprises a length between one millimeter and two millimeters.

4. The osteotome according to claim 1, wherein said replaceable tip member comprises:
   a cylindrical outer surface; and
   a shaped contour on said first end of said tip, said shaped contour configured to correspond to a contour of the cortical layer at a tooth location, for use in up-fracture of the remaining cortical bone at the tooth location.

5. The osteotome according to claim 4, further comprising a raised shape indicator on a side of said cylindrical surface, said raised shape indicator configured to provide indication of an orientation of a clocking of said shaped contour, for use in matching said shaped contour of said tip with the contour of the cortical bone.

6. The osteotome according to claim 1, wherein said first end of said tip member comprises a micro camera.

7. The osteotome according to claim 1, wherein said first end of said tip member comprises a piezo unit configured to mechanically vibrate, for use in forming a hole in the remaining cortical bone.

8. The device according to claim 1, wherein when said means for selectively receiving and measuring the fluid is toggled for said permitting of the fluid flow from said first conduit into said third conduit, the fluid is evacuated from above the sinus floor for said measuring.

9. A device for use in performing a crestal sinus membrane elevation procedure, said device comprising:
   a tip member having a first end and a second end, and comprising:
      a first conduit configured to begin at an opening at said first end and to extend in a substantially axial direction of said tip member, to terminate between said first end and said end;
      a first hydration port comprising:
         a second conduit configured to be in fluid communication with said first conduit; and
         means for releasably coupling a hose thereto, to be in fluid communication with said second conduit;
      a second hydration port comprising:
         a third conduit configured to be in selective fluid communication with said first conduit; and
         means for releasably coupling a hose thereto, to be in fluid communication with said third conduit;
   a first hose, a first end of said first hose coupled to said means for releasably coupling of said first hydration port;
   a second hose, a first end of said second hose coupled to said means for releasably coupling of said second hydration port;
   means for selectively receiving and measuring an amount of fluid, being coupled to said second end of said second hose, and configured for alternately blocking the fluid flow from said first conduit into said third conduit, and permitting and measuring the fluid flow therebetween; and
   means for infusing a measured amount of fluid, being coupled to said second end of said first hose, for infusing the measured amount of fluid through said second conduit and said first conduit, and out said opening at said first end of said tip member, above the sinus floor cortical bone to elevate the sinus membrane.

10. The device according to claim 9, wherein when said means for selectively receiving and measuring a fluid is toggled for said permitting of the fluid flow from said first conduit into said third conduit, the fluid is evacuated from above the sinus floor for said measuring.

11. An osteotome tip comprising:
   a tip member having a first end and a second end, and comprising:
      a first conduit configured to begin at an opening at said first end and to extend in a substantially axial direction, to terminate between said first end and said end;
      a second conduit in fluid communication with said first conduit;
      means for releasably coupling a hose to said tip member to be in fluid communication with said second conduit;
      a third conduit in selective fluid communication with said first conduit;
      means for releasably coupling a hose to said tip member to be in fluid communication with said third conduit;
   a first hose, a first end of said first hose coupled to said means for releasably coupling, to be in fluid communication with said second conduit;
   a second hose, a first end of said second hose coupled to said means for releasably coupling, to be in fluid communication with said third conduit;
   means for selectively receiving and measuring an amount of fluid, being coupled to said second end of said second hose, and configured for alternately blocking the fluid flow from said first conduit into said third conduit, and permitting and measuring the fluid flow therebetween; and
   means for infusing a measured amount of fluid, being coupled to said second end of said first hose, for infusing the measured amount of fluid through said second conduit and said first conduit, and out said opening at said first end of said tip member, above the sinus floor cortical bone to elevate the sinus membrane.

12. The osteotome tip according to claim 11, wherein when said means for selectively receiving and measuring a fluid is toggled for said permitting of the fluid flow from said first conduit into said third conduit, the fluid is evacuated from above the sinus floor for said measuring.

* * * * *